(12) United States Patent
Ianni et al.

(10) Patent No.: US 12,597,133 B2
(45) Date of Patent: Apr. 7, 2026

(54) TRAINING END-TO-END WEAKLY SUPERVISED NETWORKS AT THE SPECIMEN (SUPRA-IMAGE) LEVEL

(71) Applicant: PROSCIA INC., Philadelphia, PA (US)

(72) Inventors: Julianna Ianni, Philadelphia, PA (US); Saul Kohn, Philadelphia, PA (US); Sivaramakrishnan Sankarapandian, Philadelphia, PA (US); Rajath Elias Soans, Bengaluru (IN)

(73) Assignee: PROSCIA INC., Philadelphia, PA (US)

( * ) Notice: Subject to any disclaimer, the term of this patent is extended or adjusted under 35 U.S.C. 154(b) by 482 days.

(21) Appl. No.: 18/245,701

(22) PCT Filed: Sep. 17, 2021

(86) PCT No.: PCT/US2021/050828
§ 371 (c)(1),
(2) Date: Mar. 16, 2023

(87) PCT Pub. No.: WO2022/061083
PCT Pub. Date: Mar. 24, 2022

(65) Prior Publication Data
US 2023/0360208 A1      Nov. 9, 2023

Related U.S. Application Data

(60) Provisional application No. 63/080,494, filed on Sep. 18, 2020.

(51) Int. Cl.
*G06T 7/00* (2017.01)
*G06V 10/774* (2022.01)
(Continued)

(52) U.S. Cl.
CPC .......... *G06T 7/0012* (2013.01); *G06V 10/774* (2022.01); *G06V 20/70* (2022.01);
(Continued)

(58) Field of Classification Search
CPC ......... G06T 7/0012; G06T 2207/20076; G06T 2207/20081; G06T 2207/20084;
(Continued)

(56) References Cited

U.S. PATENT DOCUMENTS 10,453,197 B1    10/2019  Cholakkal et al.
10,957,041 B2 *   3/2021  Yip ........................ G06N 3/084
(Continued)

FOREIGN PATENT DOCUMENTS

CN        110309832 A      10/2019
CN        111026915 A       4/2020
(Continued)

OTHER PUBLICATIONS

Campanella et al., "Clinical-grade computational pathology using weakly supervised deep learning on whole slide images," Nature Medicine, vol. 25, No. 8, Aug. 2019 (Published online Jul. 15, 2019), pp. 1301-1309 (21 pages total).
(Continued)

*Primary Examiner* — Tom Y Lu
(74) *Attorney, Agent, or Firm* — MH2 Technology Law Group LLP

(57) ABSTRACT

Techniques for determining a presence of a pathology property in a supra-image are presented. The techniques can include receiving an electronic evaluation supra-image; providing the electronic evaluation supra-image to an electronic neural network that has been trained, using a training corpus of training supra-images and on an electronic computer, to determine the presence of the pathology property in a supra-image, each training supra-image including at least one image, each image corresponding to a plurality of components, wherein each training supra-image of the training corpus is associated with a respective electronic label indicating whether the pathology property is present, where
(Continued)

the training corpus is sufficient to train the electronic neural network to determine a presence of the pathology property; receiving from the electronic neural network an output indicative of whether the pathology property is present in the evaluation supra-image; and providing the output.

20 Claims, 11 Drawing Sheets

(51) Int. Cl.
| | |
|---|---|
| *G06V 20/70* | (2022.01) |
| *G16H 50/30* | (2018.01) |
| *G16H 70/60* | (2018.01) |

(52) U.S. Cl.
CPC ... *G16H 50/30* (2018.01); *G06T 2207/20076* (2013.01); *G06T 2207/20081* (2013.01); *G06T 2207/20084* (2013.01); *G06T 2207/30088* (2013.01); *G06T 2207/30096* (2013.01); *G06V 2201/03* (2022.01); *G16H 70/60* (2018.01)

(58) Field of Classification Search
CPC ........... G06T 2207/30088; G06T 2207/30096; G06V 10/774; G06V 20/70; G06V 2201/03; G06V 10/82; G16H 50/30; G16H 70/60; G16H 50/70; G16H 50/20; G16H 30/40; G06N 3/045; G06N 3/0895; A61B 5/055; A61B 5/7267
See application file for complete search history.

(56) References Cited

U.S. PATENT DOCUMENTS

| | | | |
|---|---|---|---|
| 11,042,807 | B2 | 6/2021 | Kapur et al. |
| 11,080,855 | B1* | 8/2021 | Beck ..................... G06V 10/82 |
| 11,308,619 | B2 | 4/2022 | Sainz De Cea et al. |
| 11,309,074 | B2 | 4/2022 | Ceballos Lentini et al. |
| 12,094,105 | B2* | 9/2024 | Matlock ................. G06V 10/26 |
| 2017/0124432 | A1 | 5/2017 | Chen et al. |
| 2019/0286880 | A1 | 9/2019 | Jackson et al. |
| 2019/0325215 | A1 | 10/2019 | Wang et al. |
| 2019/0325621 | A1 | 10/2019 | Wang et al. |
| 2019/0347847 | A1 | 11/2019 | Elgharib et al. |
| 2020/0027207 | A1 | 1/2020 | Zhang et al. |
| 2020/0058126 | A1 | 2/2020 | Wang et al. |
| 2020/0129263 | A1 | 4/2020 | Zadyyazdanabadi et al. |
| 2020/0160032 | A1 | 5/2020 | Allen et al. |
| 2020/0167972 | A1 | 5/2020 | Birnhack et al. |
| 2020/0226422 | A1 | 7/2020 | Li et al. |
| 2020/0250398 | A1 | 8/2020 | Courtiol et al. |
| 2020/0272864 | A1 | 8/2020 | Faust et al. |
| 2020/0294231 | A1 | 9/2020 | Tosun et al. |
| 2020/0342359 | A1 | 10/2020 | Hu et al. |
| 2020/0388029 | A1 | 12/2020 | Saltz et al. |
| 2020/0388033 | A1 | 12/2020 | Matlock et al. |
| 2021/0027098 | A1 | 1/2021 | Ge et al. |
| 2021/0043331 | A1 | 2/2021 | Ozcan et al. |
| 2021/0089744 | A1 | 3/2021 | Ianni et al. |
| 2021/0090250 | A1 | 3/2021 | Soans et al. |
| 2021/0166785 | A1 | 6/2021 | Yip et al. |
| 2021/0192729 | A1* | 6/2021 | Raciti .................... G06V 10/82 |
| 2021/0209760 | A1 | 7/2021 | Sue et al. |
| 2021/0217212 | A1 | 7/2021 | Birnhack et al. |
| 2021/0233251 | A1* | 7/2021 | Rothrock ............... G06N 20/00 |
| 2022/0180626 | A1* | 6/2022 | Song ..................... G16H 10/40 |
| 2023/0082179 | A1 | 3/2023 | Laradji et al. |
| 2023/0117405 | A1* | 4/2023 | Verma ................. C12Q 1/6886 382/128 |
| 2023/0245431 | A1 | 8/2023 | Ianni et al. |

FOREIGN PATENT DOCUMENTS

| | | |
|---|---|---|
| CN | 111126488 A | 5/2020 |
| WO | 2019/084697 A1 | 5/2019 |
| WO | 2020/014477 A1 | 1/2020 |
| WO | 2020/182710 A1 | 9/2020 |
| WO | 2020/193708 A1 | 10/2020 |
| WO | 2020/229585 A1 | 11/2020 |
| WO | 2022/066725 A1 | 3/2022 |
| WO | 2022/066736 A1 | 3/2022 |

OTHER PUBLICATIONS

Extended European Search Report for European Application No. 21870276.9 dated Aug. 13, 2024, 10 pages.

Jiang et al., "Image-to-image translation for automatic ink removal in whole slide images," Journal of Medical Imaging, vol. 7, No. 5, Sep./Oct. 2020 (Published online Oct. 16, 2020), pp. 057502-1-057502-14.

Extended European Search Report issued on Feb. 15, 2024, for European Application No. 21873333.5, 4 pages.

Beluch, W.H., et al., "The power of ensembles for active learning in image classification," 2018 IEEE/CVF Conference on Computer Vision and Pattern Recognition, IEEE, Jun. 18, 2018, pp. 9368-9377.

European Communication pursuant to Article 94(3) EPC (Examination Report) Issued on Apr. 4, 2023, for European Application No. 20197903.6 (6 pages).

Gupta, A., et al., "Deep Learning in Image Cytometry: A Review," Cytometry Part A, vol. 95, Issue 4, Special Issue: Image Cytometry, Apr. 2019 (Published online Dec. 19, 2018), pp. 366-380 (16 pages provided).

Leibig, C., et al., "Leveraging uncertainty information from deep neural networks for disease detection," Scientific Reports, vol. 7, Article 17816, 2017 (Published online Dec. 19, 2017), pp. 1-14.

Ji, J., "Gradient-based Interpretation on Convolutional Neural Network for Classification of Pathological Images," 2019 International Conference on Information Technology and Computer Application (ITCA), IEEE, 2019, pp. 83-86 (retrieved from the internet on Nov. 21, 2021), <URL: https://ieeexplore.ieee.org/stamp/stamp.jsp?tp=&arnumber=9092504>.

International Search Report and Written Opinion of the International Searching Authority dated Dec. 22, 2021 in International Apln. No. PCT/US2021/051495, 8 pages.

International Search Report and Written Opinion of the International Searching Authority dated Dec. 17, 2021 in International Apln. No. PCT/US2021/050828, 10 pages.

International Search Report and Written Opinion of the International Searching Authority dated Dec. 27, 2021 in International Apln. No. PCT/US2021/051506, 9 pages.

Samsi, S., et al., "Colorization of H&E stained tissue using Deep Learning," 2018 40th Annual International Conference of the IEEE Engineering in Medicine and Biology Society (EMBC), IEEE, 2018, pp. 640-643.

Tellez, D., et al., "Quantifying the effects of data augmentation and stain color normalization in convolutional neural networks for computational pathology," arXiv:1902.06543v1 [cs.CV], Feb. 18, 2019, pp. 1-12.

Extended European Search Report issued on Feb. 12, 2021 in European Apln. No. 20197904.4, 8 pages.

Yuan, E., et al., "Neural Stain Normalization and Unsupervised Classification of Cell Nuclei in Histopathological Breast Cancer Images," arXiv:1811.03815v1 [cs.CV], Nov. 9, 2018, pp. 1-9.

Zhang, R., et al., "Colorful Image Colorization," arXiv:1603.08511v5 [cs.CV], Oct. 5, 2016, pp. 1-29.

Extended European Search Report issued on Feb. 8, 2021 in European Apln. No. 20197903.6 , 9 pages.

Gal, Y., et al., "Dropout as a Bayesian Approximation: Representing Model Uncertainty in Deep Learning," Proceedings of the 33rd International Conference on Machine Learning, vol. 48, 2016, 10 pages.

(56) References Cited

OTHER PUBLICATIONS

"Notice of Allowance and PTO-892 listing of prior art form," issued Jun. 24, 2022 in related U.S. Appl. No. 17/028,069, entitled "Automated Whole-Slide Image Classification Using Deep Learning," filed Sep. 22, 2022.

Lu et al., "Deep Learning-based Computational Pathology Predicts Origins for Cancers of Unknown Primary," arXiv:2006.13932v2 [q-bio.TO] Jun. 29, 2020, 33 pages.

Sun et al., "Computer-Aided Diagnosis in Histopathological Images of the Endometrium Using a Convolutional Neural Network and Attention Mechanisms," IEEE Journal of Biomedical and Health Informatics, vol. 24, Issue 6, Jun. 5, 2020, pp. 1664-1676.

* cited by examiner

TRAINING END-TO-END WEAKLY SUPERVISED NETWORKS AT THE SPECIMEN (SUPRA-IMAGE) LEVEL

RELATED APPLICATION

This application is a 35 USC § 371 national stage entry of PCT/2021/050828, filed Sep. 17, 2021, and entitled "Training End-To-End Weakly Supervised Networks at the Specimen (Supra-Image) Level," which claims priority to, and the benefit of, U.S. Provisional Patent Application No. 63/080,494, filed Sep. 18, 2020, and entitled "Training End-To-End Weakly Supervised Networks at the Specimen (Supra-Image) Level," both which are hereby incorporated by reference herein in their entireties.

FIELD

This disclosure relates generally to machine learning, e.g., in the context of pathology, such as dermatopathology.

BACKGROUND

Much recent research has advanced the application of deep learning techniques for classification problems in digital pathology, satellite imaging, and other fields that use gigapixel images with weak labels (e.g., labels at the level of the supra-image). While until recently, deep learning techniques for these applications required time-consuming pixel-wise annotations of positive regions of interest within these images for training, now multiple-instance learning techniques allow division of one or several images into patches or tiles, which are then treated as instances or components when training neural networks in this paradigm; but one label at an image, or specimen (or supra-image, comprising several images) level is required.

Ignoring the connection of the constituent images that form a supra-image and simply using them separately to train a machine learning classifier produces inaccurate and unsatisfactory results. A weak label provides information for its supra-image, rather than the individual constituent images. Labelling constituent images with the weak label from their supra-image and using them separately can introduce noise into the training process, because one constituent image may contain no features relevant to its label.

SUMMARY

According to various embodiments, a computer-implemented method of determining a presence of a pathology property in a supra-image is presented. The method includes: receiving an electronic evaluation supra-image; providing the electronic evaluation supra-image to an electronic neural network that has been trained, using a training corpus of training supra-images and on an electronic computer, to determine the presence of the pathology property in a supra-image, each training supra-image including at least one image, each image corresponding to a plurality of components, where each training supra-image of the training corpus is associated with a respective electronic label indicating whether the pathology property is present, where the training corpus is sufficient to train the electronic neural network to determine a presence of the pathology property; receiving from the electronic neural network an output indicative of whether the pathology property is present in the evaluation supra-image; and providing the output.

Various optional features of the above embodiments include the following. The electronic computer can include volatile electronic memory having a storage capacity, where a probability that the pathology property is present in at least one component of a sampled collection of components of images of at least one training supra-image of the training corpus indicates that the training corpus is sufficient to train the electronic neural network to determine the presence of the pathology property, where the storage capacity of the volatile electronic memory is sufficient to store the sampled collection of components simultaneously. The method can include obtaining, for each respective component of each image of the at least one training supra-image of the training corpus, a respective electronic label indicating whether the pathology property is present in the respective component, whereby a plurality of labels is obtained; where the probability is based on at least the plurality of labels. The method can include calculating, based on at least the plurality of labels, the probability; and determining, based on at least the probability, that the training corpus is sufficient to train the electronic neural network to determine the presence of the pathology property. The probability can include $$1 - \frac{n_{neg}! \, (N - n_{RAM})!}{N! \, (n_{neg} - n_{RAM})!},$$

where $N$ represents a number of components of the sampled collection of components, $n_{neg}$ represents a number of components of the sampled collection of components that lack the pathology property, and $n_{RAM}$ represents a maximum number of components that can be simultaneously stored in the volatile electronic memory. The electronic neural network can have been trained, using the training corpus of training supra-images and on an electronic computer, to determine the presence of the pathology property in a supra-image by: randomly sampling collections of components corresponding to images from individual training supra-images, whereby a plurality of collections of components are obtained; labeling the collections of components according to a respective electronic label for their respective supra-image, whereby a plurality of weakly labeled collections of components are obtained from the plurality of collections of components; iteratively training, through the plurality of weakly labeled collections of components, the electronic neural network to determine the presence of the pathology property. The evaluation supra-image and a plurality of the training supra-images can represent biopsies. Each image of a plurality of the training supra-images can include a whole-slide image, where the evaluation supra-image includes at least one whole-slide image. Each component can a feature vector. The pathology property can include one of: a presence of a malignancy, a presence of a specific grade of malignancy, or a presence of a category of risk.

According to various embodiments, a system for determining a presence of a pathology property in a supra-image is presented. The system includes: a processor; and a memory communicatively coupled to the processor, the memory storing instructions which, when executed on the processor, perform operations including: receiving an electronic evaluation supra-image; providing the electronic evaluation supra-image to an electronic neural network that has been trained, using a training corpus of training supra-images and on an electronic computer, to determine the presence of the pathology property in a supra-image, each

3 training supra-image including at least one image, each image corresponding to a plurality of components, where each training supra-image of the training corpus is associated with a respective electronic label indicating whether the pathology property is present, where the training corpus is sufficient to train the electronic neural network to determine a presence of the pathology property; receiving from the electronic neural network an output indicative of whether the pathology property is present in the evaluation supra-image; and providing the output.

Various optional features of the above embodiments include the following. The electronic computer can include volatile electronic memory having a storage capacity, where a probability that the pathology property is present in at least one component of a sampled collection of components of images of at least one training supra-image of the training corpus indicates that the training corpus is sufficient to train the electronic neural network to determine the presence of the pathology property, where the storage capacity of the volatile electronic memory is sufficient to store the sampled collection of components simultaneously. The operations can further include: obtaining, for each respective component of each image of the at least one training supra-image of the training corpus, a respective electronic label indicating whether the pathology property is present in the respective component, whereby a plurality of labels is obtained; where the probability is based on at least the plurality of labels. The operations can further include: calculating, based on at least the plurality of labels, the probability; and determining, based on at least the probability, that the training corpus is sufficient to train the electronic neural network to determine the presence of the pathology property. The probability can include $$1 - \frac{n_{neg}! \, (N - n_{RAM})!}{N! \, (n_{neg} - n_{RAM})!},$$

where N represents a number of components of the sampled collection of components, $n_{neg}$ represents a number of components of the sampled collection of components that lack the pathology property, and $n_{RAM}$ represents a maximum number of components that can be simultaneously stored in the volatile electronic memory. The electronic neural network can have been trained, using the training corpus of training supra-images and on an electronic computer, to determine the presence of the pathology property in a supra-image by: randomly sampling collections of components corresponding to images from individual training supra-images, whereby a plurality of collections of components are obtained; labeling the collections of components according to a respective electronic label for their respective supra-image, whereby a plurality of weakly labeled collections of components are obtained from the plurality of collections of components; iteratively training, through the plurality of weakly labeled collections of components, the electronic neural network to determine the presence of the pathology property. The evaluation supra-image and a plurality of the training supra-images can represent biopsies. Each image of a plurality of the training supra-images can include a whole-slide image, where the evaluation supra-image includes at least one whole-slide image. Each component can include a feature vector. The pathology property can include one of: a presence of a malignancy, a presence of a specific grade of malignancy, or a presence of a category of risk.

4

BRIEF DESCRIPTION OF DRAWINGS

The above and/or other aspects and advantages will become more apparent and more readily appreciated from the following detailed description of examples, taken in conjunction with the accompanying drawings, in which.

DESCRIPTION OF THE EMBODIMENTS

Reference will now be made in detail to example implementations. These embodiments are described in sufficient detail to enable those skilled in the art to practice the invention and it is to be understood that other embodiments may be utilized and that changes may be made without departing from the scope of the invention. The following description is, therefore, merely exemplary.

I. Introduction

Embodiments can use weakly-labeled supra-images to train a machine learning algorithm, such as an electronic neural network, in a manner that provides superior classification results in comparison to existing techniques. Embodiments may be applied to provide pathology classifications in the medical field, to classify features in satellite images, or in any other field that involves detecting and/or classifying features in sets of images.

Figure 1:
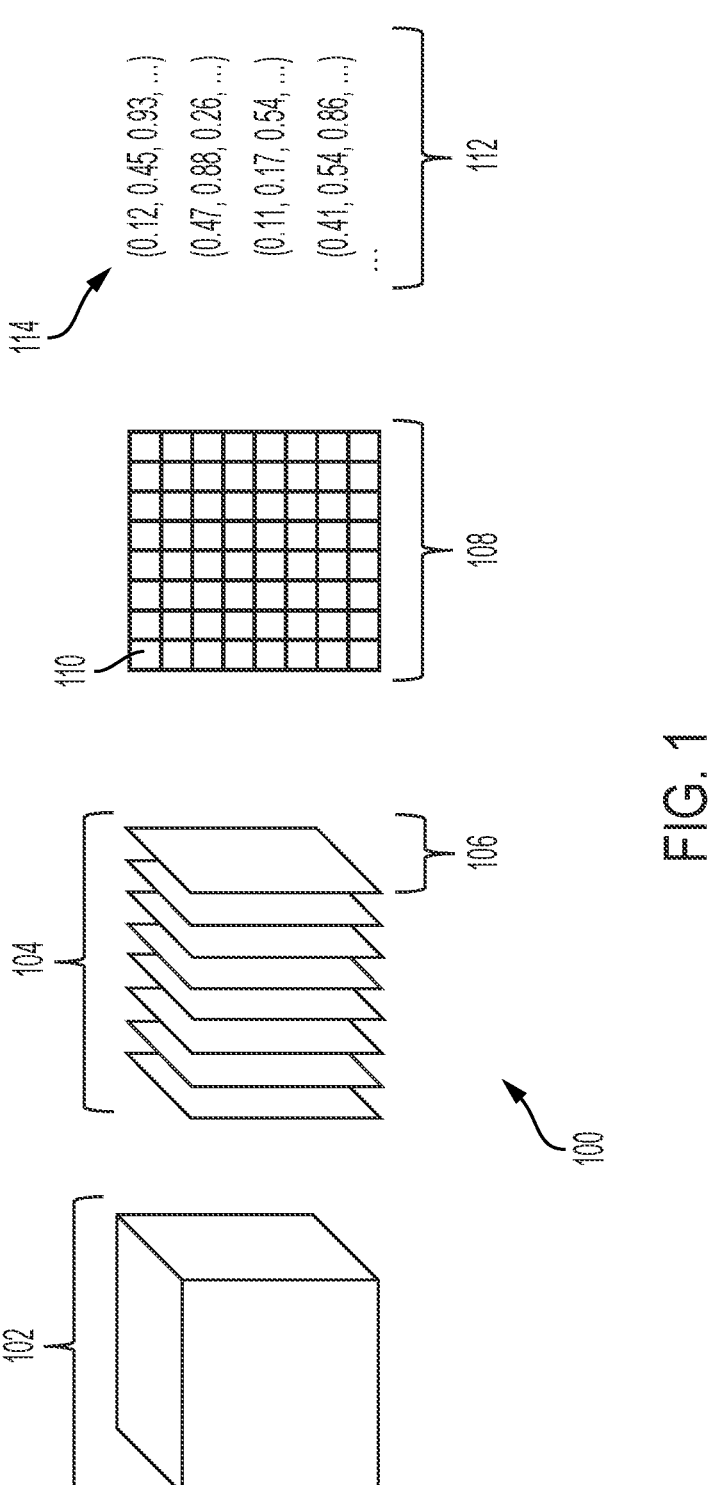
FIG. 1 is a schematic diagram depicting an example supra-image, its constituent images, a tiling of one of its constituent images, and vector representations of the tiles of the constituent image according to various embodiments.

FIG. 1 is a schematic diagram 100 depicting an example supra-image 102, its constituent images 104, a tiling 108 of one of its constituent images 106, and vector representations 112 of the tiles of the constituent image 106 according to various embodiments. As used herein, the term "supra-image" includes one or more constituent images of a specimen. The specimen may be a medical specimen, a landscape specimen, or any other specimen amenable to image capture.

For example, a supra-image may represent images from a single resection or biopsy (the supra-image) constituting several slides (the constituent images). As another example, the supra-image may be a three-dimensional volume representing the results of a radiological scan, and the constituent images may include two-dimensional slices of the three-dimensional volume. Within the domain of digital pathology, the images forming a supra-image may be of tissue stained with Hematoxylin and Eosin (H&E), and a label may be associated with the supra-image, for example, the diagnosis rendered by the pathologist. Frequently, more tissue is cut than can be scanned in a single slide—this is especially frequent for suspected malignant cases—and several images may share the same weak label. A supra-image may be of any type of specimen in any field, not limited to pathology, e.g., a set of satellite images.

As shown in, FIG. 1, supra-image 102 may represent a three-dimensional volume by way of non-limiting examples. Supra-image 102 may be, for example, a representation of a three-dimensional Computer Tomography (CT) or Magnetic Resonance Imaging (MRI) scan. Images 104 represent the constituent images of supra-image 102. By way of non-limiting examples, images 104 may be slices derived from, or used to derive, a CT or MRI scan, or may be whole-slide images, e.g., representing multiple images from a biopsy of a single specimen.

In general, when processed by a computer, due to hardware volatile memory storage limitations, each constituent image of a supra-image may be broken down into a number of tiles, which may be, e.g., 128 pixels by 128 pixels. As shown in FIG. 1, image 106 of constituent images 104 may be partitioned into tiles, such as tile 110, to form partitioned image 108.

In general, an individual tile may be represented by one or more corresponding feature vectors. Such feature vectors may be obtained from tiles using a separate neural network, trained to produce feature vectors from tiles. Each such feature vector may encode the presence or absence of one or more features in the tile that it represents. Each feature vector may be in the form of a tuple of numbers. As shown in FIG. 1, feature vectors 112 represent the tiles of partitioned image 108. For example feature vector 114 may correspond to and represent a presence or absence of a particular feature in tile 110.

Both tiles and their representative feature vectors are examples of "components" as that term is used herein. According to some embodiments, each component is implemented as a tile of a constituent image of a supra-image. According to some embodiments, each component is implemented as a vector, such as a feature vector, that represents a respective tile in a constituent image of a supra-image.

While previous work in multiple-instance learning has been limited to training at the level of small image patches, or subsets of an image identified by a pre-processing step or network, this disclosure extends tile-based multiple-instance learning training to the supra-image level, which does not require selecting out small regions of interest.

II. Description of the Problem

Datasets that contain large numbers of high-resolution images, such as neural network training corpora, can be extremely costly to annotate in detail. A time-saving and cost-saving alternative to annotations is to supply weak labels to the images or supra-images, simply stating whether or not certain features are present.

In past work, weakly-supervised networks were trained to operate either only in the specific case of a weak label per-image, or using a downstream classifier or alternative numerical method to combine the output of a weakly-supervised classifier from the image level to the supra-image level. The former case clearly restricts the usability of a trained network, while the latter relies on two models' or methods' performance to generate and combine image-level classifications to produce a representative supra-image level classification.

None of these prior methods of artificial intelligence training allow for training based on how diagnoses are made in clinical practice, where the pathologist renders a diagnosis for each specimen only, not for each individual slide pertaining to that specimen. This diagnosis may be stored in an electronic clinical records system, such as a Laboratory Information System ("LIS"), a Laboratory Information Management System ("LIMS"), an Electronic Medical Record ("EMR") system. By abstracting training to the specimen level, some embodiments provide a training method that may operate on diagnoses made straight from an electronic clinical records system, without the requirement of human intervention to label relevant slides. That is, some embodiments may use as a training corpus of supra-images with weak labels taken from diagnoses stored in an electronic clinical records system.

While embodiments may be applied within the domain of digital pathology, the supra-image methods disclosed herein generalize to other fields with problems that involve several images with shared labels, such as time series of satellite images.

III. Description of Example Embodiments

Some embodiments train neural networks in a weakly-supervised fashion, using collections of components from images constituting supra-images as the input data, with a single label per collection. Moreover, some embodiments determine whether a weakly-labeled training corpus is sufficient for accurately training a neural network.

Current hardware (e.g., Graphical Processing Units or GPUs) commonly used to train neural networks cannot always hold all the image tiles from a supra-image or constituent image at once due to Random Access Memory (RAM) limitations. For example, each image of a supra-image is typically too large to feed into the hardware used to hold and train the deep learning neural network. Some embodiments train a weakly supervised neural network at the supra-image level, within these hardware limitations, by sampling (e.g., randomly sampling) components from constituent images of supra-images into collections of components that are close to the maximum size the hardware is able to hold in RAM.

The random sampling may not take into account which image from a supra-image the components are drawn from; components may be randomly drawn without replacement from a common pool for the supra-image. The sampling can be performed several times for a given supra-image, creating more than one collection to train with for a given supra-image. Multiple such collections may form a partition of a given supra-image; that is, the set-theoretic union of the collections from a single supra-image may cover the entire supra-image, and the set-theoretic intersection of such collections may be empty.

Some embodiments provide a framework in which each image in a supra-image is divided into a mosaic of tiles, e.g., squares of 128 pixels-per-side. A sampled collection of such tiles, or feature vector representations thereof, small enough to be stored in the available volatile memory of the training computer, and labeled with the label of the supra-image from which the tiles are obtained, may serve as a single element of the training corpus for weakly-supervised training according to various embodiments. Multiple such labeled collections of components may comprise a full training corpus. No region-of-interest need be identified. Some embodiments determine whether a training corpus is sufficient for training a neural network to accurately classify novel supra-images.

Figure 2:
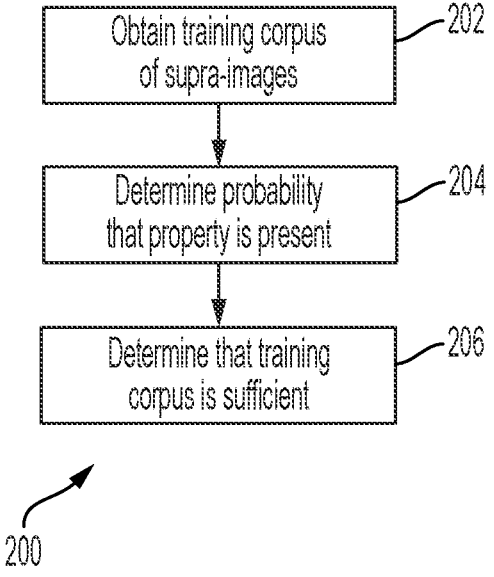
FIG. 2 is a flow diagram for a method of determining the sufficiency of a training corpus to train a neural network, at the supra-image level, to classify supra-images for the presence of a property according to various embodiments.

FIG. 2 is a flow diagram for a method of determining the sufficiency of a training corpus to train a neural network, at the supra-image level, to classify supra-images for the presence of a property according to various embodiments. For example, method 200 may be used to determine whether a neural network trained using a particular training corpus of supra-images will accurately classify a novel supra-image as including or not including a property of interest. The property of interest may be any detectable property. By way of non-limiting examples, in the dermatopathological domain, the property may be the presence of any of: malignant melanoma, basal cell carcinoma, dermal nevus, or seborrheic keratosis. In the domain of satellite imagery, the property of interest may be the presence of a particular type of structure, vehicle, or ordnance. Method 200 may be implemented by system 500, as shown and described herein in reference to FIG. 5.

At 202, method 200 obtains a training corpus of supra-images. Each supra-image is weakly labeled, or may be weakly labeled, with information denoting whether or not the property is present, e.g., whether property of interest in is present in one or more of its constituent images, or absent from all of its constituent images. Method 200 may obtain the training corpus of supra-images from a variety of sources and in a variety of ways. For example, the supra-images and labels may be obtained from an electronic clinical records system, such as an LIS. The supra-images maybe obtained over a network communication link, or by retrieval from electronic persistent memory, by way of non-limiting examples. The training corpus may include hundreds, thousands, or even tens of thousands or more supra-images.

At 204, method determines a probability that a property, e.g., a pathology property, is present in a supra-image in the training corpus. In general, given an annotated supra-image, it is possible to calculate the probability of a component (e.g., tile or feature vector) that is positive for the property of interest being present in a sampled collection (e.g., randomly sampled) of components as follows. For a supra-image with N total tiles, where $N=n_{neg}+n_{pos}$; $n_{neg}$ and $n_{pos}$ corresponding to the numbers of negative components and positive components, respectively, and a maximum number of tiles to be held in RAM $n_{RAM}$, the probability p of at least one positive component being present in the tiles held in RAM may be represented as, by way of non-limiting example:

$$p = 1 - \frac{n_{neg}! \, (N - n_{RAM})!}{N! \, (n_{neg} - n_{RAM})!} \quad (1)$$

The computation of p may be extrapolated to a small number of supra-images and their respective collections of components. For example, p may be computed for a sampled portion of a training corpus and extrapolated to the entire training corpus using known statistical techniques. Thus, the actions of 204 can include randomly sampling supra-images from the training corpus and determining a confidence, based on the random samples, that the computation of p from the random samples applies to the overall training corpus. To that end, known statistical methods may be used to sample a small number of supra-images from the training corpus and compute p from the sampled supra-images, and then extrapolate the value of p (e.g., plus or minus a specified margin of error) to the entire training corpus with a known level of confidence. For example, a small number (e.g., 20) supra-images may be randomly sampled from a training corpus of a large number (e.g., 5000) of supra-images, and p may be computed from the sample (e.g., p=0.85). Known statistical methods may be applied to determine that the computation of p is accurate to within some error margin (e.g., within ±0.05) with a known confidence level (e.g., 70%). The example specific numbers provided in the preceding example are intended to be illustrative rather than the results of a single specific determination.

At 206, method 200 determines whether the training corpus is sufficient to train a neural network to accurately determine the presence of a property in a supra-image. For example, if the average value of p across the annotated supra-image(s) as determined at 204 is close to one, weakly-supervised training may proceed as expected and training should be stable. Average values of p that are not close to one, but still above 0.5 will cause noisier training, but may still allow the network to learn, because the majority of collections will contain at least one positive component. Thus, the calculation of p may be used to get a justification for the supra-image-level approach for a given problem. According to some embodiments, if p is within a particular error margin of a particular probability with a particular confidence, then the training corpus is sufficient. Values for the particular probability include 0.5, 0.6, 0.7, 0.9, and 0.95. Values for the particular error margin include 0.001, 0.01, 0.05, 0.1, and 0.2. Values for the particular confidence include 0.6, 0.7, 0.8, 0.9, and 0.95. Any of the preceding values of the particular probability, particular error margin, and particular confidence may be used in any combination according to various embodiments.

Thus, some embodiments compute or estimate p for one or more representative labeled supra-images, determine that p is sufficiently large for the one or more supra-images and/or the full set of supra-images from which the one or more labeled supra-images are drawn, and then, as described further below, obtain multiple labeled randomly sampled collections of components from the images that make up such supra-images. The supra-images form a training corpus from which such multiple labeled collections from the supra-images for individual training units. The training corpus may be used to train a neural network, which may then be used to classify a newly-presented supra-image.

Figure 3:
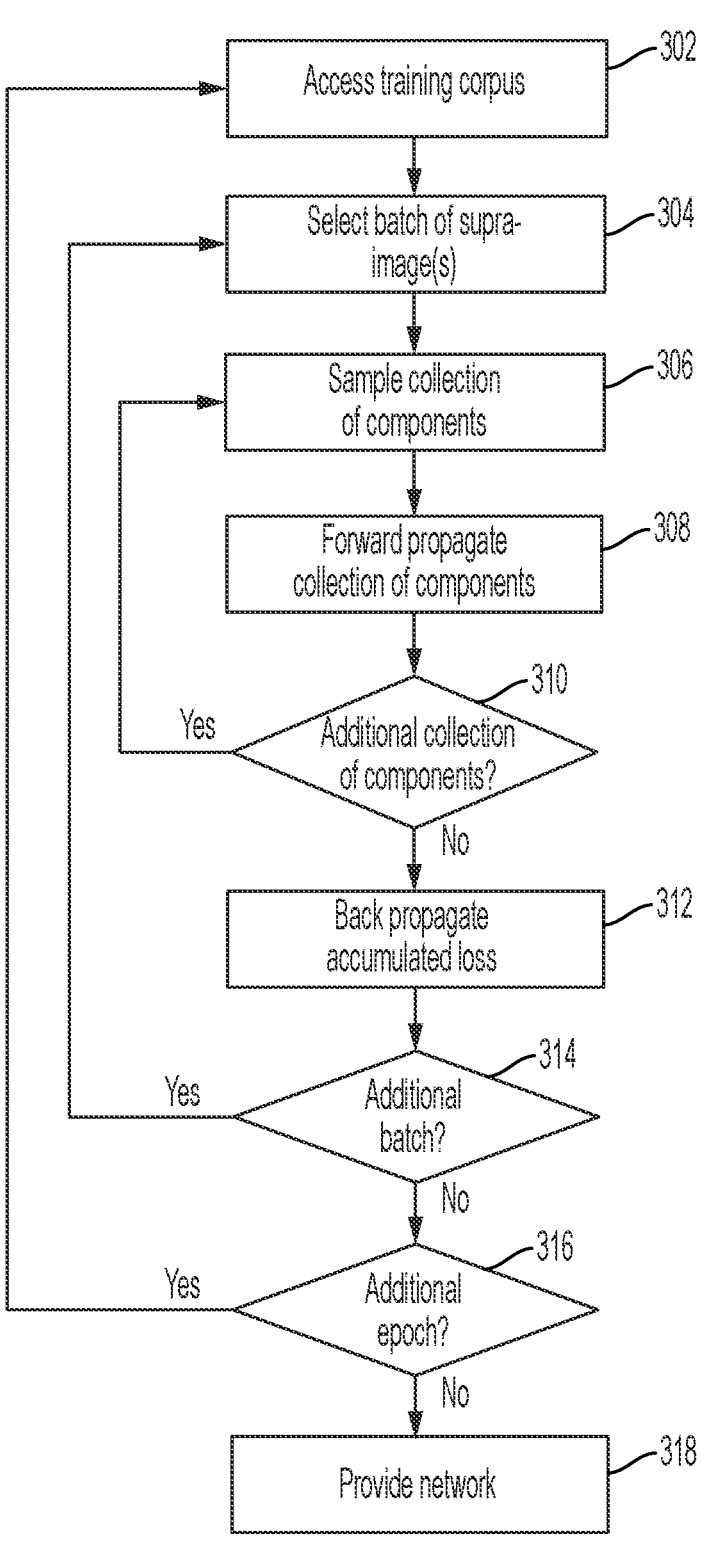
FIG. 3 is a flow diagram for a method of iteratively training, at the supra-image level, a neural network to classify supra-images for the presence of a property according to various embodiments.

FIG. 3 is a flow diagram for a method 300 of iteratively training, at the supra-image level, a neural network to classify supra-images for the presence of a property according to various embodiments. Method 300 may be practiced after method 200 of FIG. 2 has been employed to determine that the training corpus of supra-images accessed per 302 is sufficient. Method 300 may be implemented by system 500, as shown and described herein in reference to FIG. 5.

At block 302, method 300 accesses a training corpus of supra-images. The supra-images may be in any field of interest. The supra-images include or may be otherwise associated with weak labels. The supra-images and weak labels may be obtained from an electronic clinical records system, such as an LIS. The supra-images maybe accessed over a network communication link, or from electronic persistent memory, by way of non-limiting examples. The training corpus may include hundreds, thousands, or even tens of thousands or more supra-images. The training corpus of supra-images may have previously been determined to be sufficient, e.g., by employing method 200 as shown and described herein in reference to FIG. 2.

At 304, method 300 selects a batch of supra-images for processing. In general, the training corpus of supra-images with supra-image level labels to be used for training is divided into one or more batches of one or more supra-images. In general, during training, the loss incurred by the network is computed over all batches through the actions of 304, 306, 308, 310, 312, and 314. The losses over all of the batches are accumulated, and then the weights and biases of the network are updated, at which point the accumulated loss is reset, and the process repeats until the iteration is complete.

At 306, method 300 samples, e.g., randomly samples, a collection of components from the batch of supra-images selected at 304. In general, each batch of supra-images is identified with a respective batch of collections of components, where each collection of components includes one or more components sampled, e.g., randomly sampled, from one or more images from a single supra-image in the batch of supra-images. Thus, the term "batch" may refer to both a batch of one or more supra-images and a corresponding batch of collections of components from the batch of one or more supra-images. Embodiments may not take into account which constituent image a given component in a collection comes from; components in the collection may be randomly drawn without replacement from a common pool for a given supra-image. Each collection of components is labeled according to the label of the supra-image making up the images from which the components from the collection are drawn. The components may be tiles of images within the selected supra-image batch, or may be feature vectors representative thereof. The collections of components, when implemented as tiles, may form a partition of a given supra-image, and when implemented as vectors, the corresponding tiles may form a partition.

Embodiments may iterate through a single batch, i.e., a batch of collections of components, through the actions of 306, 308, and 310, until all components from the images of the supra-images for the batch are included in some collection of components that is forward propagated through the network. Embodiments may iterate through all of the batches through the actions of 304, 306, 308, 310, 312, and 314 to access the entire training dataset to completely train a network.

Thus, at 308, the collection of components sampled at 306 is forward propagated through the neural network to compute loss. When the collection of components that is forward propagated through the multiple-instance learning neural network, the network's prediction is compared to the weak label for the collection. The more incorrect it is, the larger the loss value. Such a loss value is accumulated each time a collection of components is propagated through the network, until all collections of components in the batch are used.

At 310, method 300 determines whether there are additional collections of components from the batch selected at 304 that have not yet been processed. If so, control reverts to 306, where another collection of components is selected for processing as described above. If not, then control passes to 312.

At 312, method 300 back propagates the accumulated loss to update the weights and biases of the neural network. That is, after iterating through the collections of components from a single batch, the neural network weights and biases are updated according to the magnitude of the aggregated loss. This process repeats over all batches in the dataset.

Thus, at 314, method 300 determines whether there are additional batches of supra-images from the training corpus accessed at 302 that have not yet been processed during the current iteration. Embodiments may iterate over the batches to access the entire training dataset. If additional batches exist, then control reverts to 304, where another batch of one or more supra-images is selected. Otherwise, control passes to 316.

At 316, once all collections of components from all batches of supra-images are processed according to 304, 306, 308, 310, 312, and 314, a determination is made as to whether an additional epoch is to be performed. In general, each iteration over all batches of supra-images in the training corpus may be referred to as an "epoch". Embodiments may train the neural networks for hundreds, or even thousands or more, of epochs.

At 318, method 300 provides the neural network that has been trained using the training corpus accessed at 302. Method 300 may provide the trained neural network in a variety of ways. According to some embodiments, the trained neural network is stored in electronic persistent memory. According to some embodiments, the neural network is made available on a network, such as the internet. According to some such embodiments, an interface to the trained neural network is provided, such as a Graphical User Interface (GUI) or Application Program Interface (API).

Figure 4:
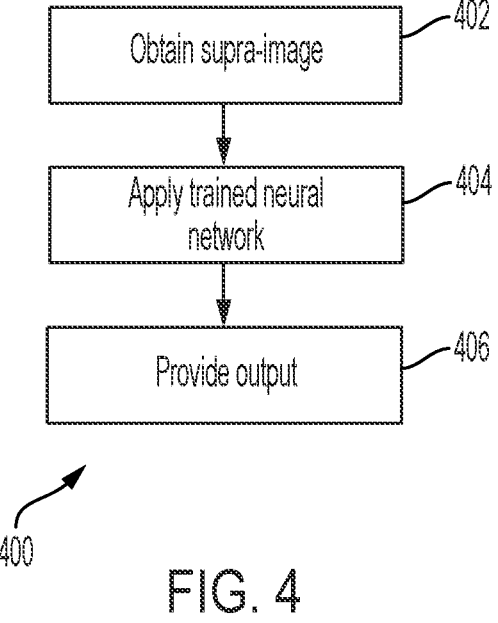
FIG. 4 is a flow diagram for a method of automatically classifying a supra-image according to various embodiments.

FIG. 4 is a flow diagram for a method 400 of automatically classifying a supra-image according to various embodiments. Method 400 may use a neural network trained according to method 300 as shown and described herein in reference to FIG. 3. Method 200 may be implemented by system 500, as shown and described herein in reference to FIG. 5.

At 402, a supra-image is obtained. The supra-image may be in any field. The supra-image may be obtained over a network link or by retrieval from persistent storage, by way of non-limiting example.

At 404, the neural network is applied to the supra-image obtained at 402. To do so, the supra-image may be broken down into parts (e.g., components or sets of components) and the parts may be individually passed through the network up to a particular layer, where the features from the various parts are aggregated, and then the parts are passed through to a further particular layer, where the features are again aggregated, until all parts are passed and all features aggregated such that one or more outputs are produced. Multiple outputs, if present, may be independently useful, or may be synthesized to produce a final, single output.

At 406, method 400 provides the output. The output may be provided by displaying a corresponding datum to a user of method 400, e.g., on a computer monitor. Such a datum may indicate the presence or absence of the feature of interest in the supra-image.

Figure 5:
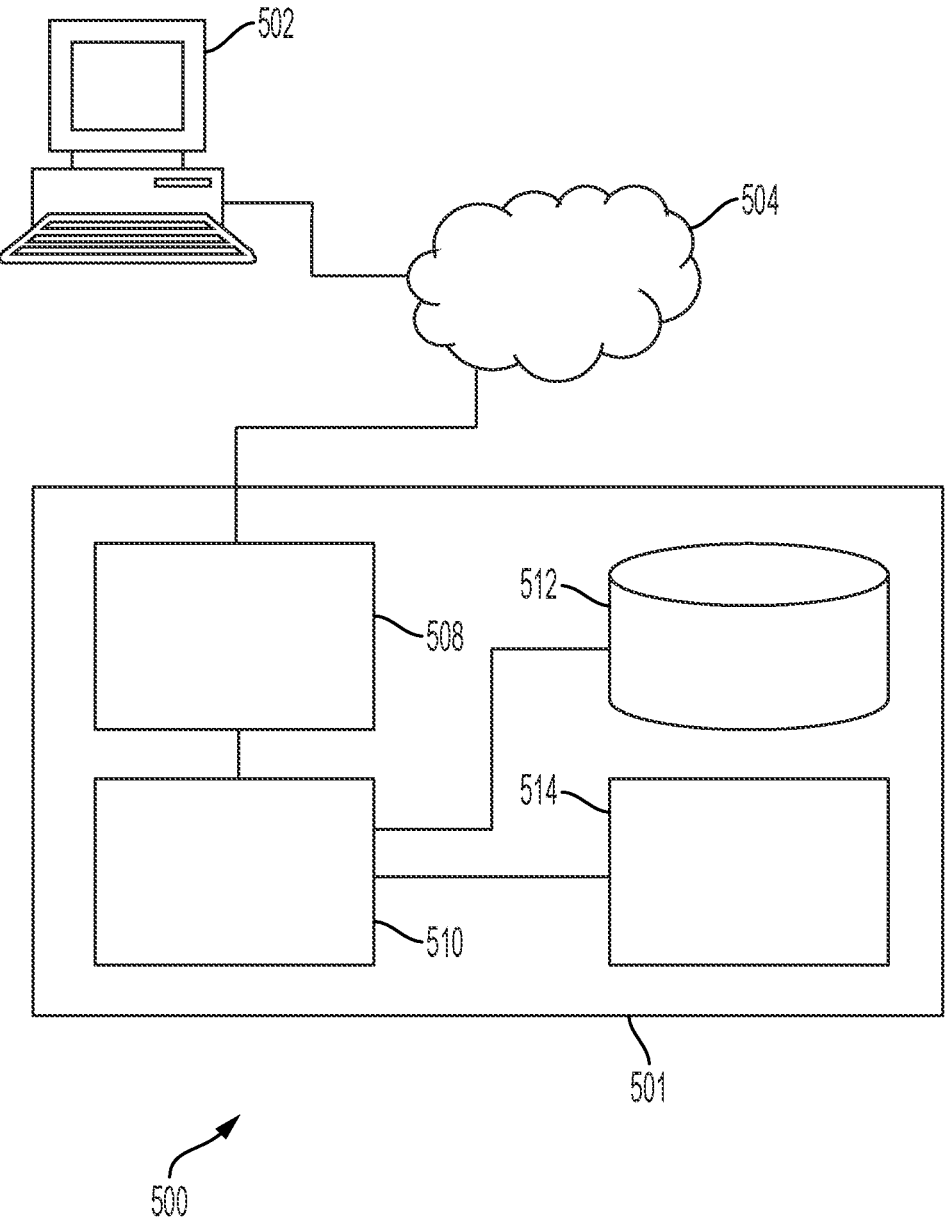
FIG. 5 is a schematic diagram of a hardware computer system suitable for implementing various embodiments.

FIG. 5 is a schematic diagram of a hardware computer system 500 suitable for implementing various embodiments. For example, FIG. 5 illustrates various hardware, software, and other resources that can be used in implementations of method 200 as shown and described herein in reference to FIG. 2, method 300 as shown and described herein in reference to FIG. 3, and/or method 400 as shown and described herein in reference to FIG. 4. System 500 includes training corpus source 520 and computer 501. Training corpus source 520 and computer 501 may be communicatively coupled by way of one or more networks 504, e.g., the internet.

Training corpus source 502 may include an electronic clinical records system, such as an LIS, a database, a compendium of clinical data, or any other source of supraimages suitable for use as a training corpus as disclosed herein.

Computer 501 may be implemented as any of a desktop computer, a laptop computer, can be incorporated in one or more servers, clusters, or other computers or hardware resources, or can be implemented using cloud-based resources. Computer 501 includes volatile memory 514 and persistent memory 512, the latter of which can store computer-readable instructions, that, when executed by electronic processor 510, configure computer 501 to perform any of methods 200, 300, and/or 400, as shown and described herein. Computer 501 further includes network interface 508, which communicatively couples computer 501 to training corpus source 502 via network 504. Other configurations of system 500, associated network connections, and other hardware, software, and service resources are possible.

IV. Example Reduction to Practice

This Section presents an example reduction to practice. The example reduction to practice is configured to perform hierarchical classification of digitized whole-slide image specimens into six classes defined by their morphological characteristics, including classification of "Melanocytic Suspect" specimens likely representing melanoma or severe dysplastic nevi. The reduction to practice was trained on 7,685 images from a single lab (the reference lab), including the largest set of triple-concordant melanocytic specimens compiled to date, and tested the system on 5,099 images from two distinct validation labs. The reduction to practice achieved Area Underneath the Receiver Operating Characteristics Curve (AUC) values of 0.93 classifying Melanocytic Suspect specimens on the reference lab, 0.95 on the first validation lab, and 0.82 on the second validation lab. The reduction to practice is capable of automatically sorting and triaging skin specimens with high sensitivity to Melanocytic Suspect cases and demonstrates that a pathologist would only need between 30% and 60% of the caseload to address all melanoma specimens.

A. Introduction to the Reduction to Practice

More than five million diagnoses of skin cancer are made each year in the United States, about 106,000 of which are melanoma of the skin. Diagnosis requires microscopic examination H&E stained, paraffin wax embedded biopsies of skin lesion specimens on glass slides. These slides can be manually observed under a microscope, or digitally on a whole-slide image scanned on specialty hardware.

The five-year survival rate of patients with metastatic malignant melanoma is less than 20%. Melanoma occurs more rarely than several other types of skin cancer, and its diagnosis is challenging, as evidenced by a high discordance rate among pathologists when distinguishing between melanoma and benign melanocytic lesions (~40% discordance rate). The Melanocytic Pathology Assessment Tool and Hierarchy for Diagnosis (MPATH-Dx; "MPATH" hereafter) reporting schema was introduced by Piepkorn, et al., *The mpath-dx reporting schema for melanocytic proliferations*

*and melanoma*, Journal of the American Academy of Dermatology, 70(1):131-141, 2014 to provide a precise and consistent framework for dermatopathologists to grade the severity of melanocytic proliferation in a specimen. MPATH scores are enumerated from I to V, with I denoting a benign melanocytic lesion and V denoting invasive melanoma. It has been shown that discordance rates are related to the MPATH score, with better inter-observer agreement on both ends of the scale than in the middle.

A tool that allows labs to sort and prioritize melanoma cases in advance of pathologist review could improve turnaround time, allowing pathologists to review cases requiring faster turnaround time early in the day. This is particularly important as shorter turnaround time is correlated with improved overall survival for melanoma patients. It could also alleviate common lab bottlenecks such as referring cases to specialized dermatopathologists, or ordering additional tissue staining beyond the standard H&E. These contributions are especially important as the number of skin biopsies performed per year has skyrocketed, while the number of practicing pathologists has declined.

The advent of digital pathology has brought the revolution in machine learning and artificial intelligence to bear on a variety of tasks common to pathology labs. Several deep learning algorithms have been introduced to distinguish between different skin cancers and healthy tissue with very high accuracy. See, e.g., De Logu, et al, *Recognition of cutaneous melanoma on digitized histopathological slides via artificial intelligence algorithm*, Frontiers in Oncology, 10, 2020; Thomas, et al, *Interpretable deep learning systems for multi-class segmentation and classification of nonmelanoma skin cancer*, Medical Image Analysis, 68:101915, 2021; Zormpas-Petridis, et al., *Superhistopath: A deep learning pipeline for mapping tumor heterogeneity on low-resolution whole-slide digital histopathology images*, Frontiers in Oncology, 10:3052, 2021; and Geijs, et al., *End-to-end classification on basal-cell carcinoma histopathology whole-slides images*, Society of Photo-Optical Instrumentation Engineers (SPIE) Conference Series, February 2021. However, almost all of these studies fail to demonstrate the robustness required for use in a clinical workflow setting because they were tested a on small number (<~1000) of whole-slide images. Moreover, these algorithms are often not capable of triaging whole-slide images, as they use curated training and test datasets that do not represent the diversity of cases encountered in a dermatopathology lab. Many of them rely on pixel-level annotations to train their models, which is slow and expensive to scale to a large dataset with greater variability.

Considerable advancements have been made towards systems capable of use in clinical practice for prostate cancer. In Campanella, et al., *Clinical-grade computational pathology using weakly supervised deep learning on whole-slide images*, Nature Medicine, 25(8):1301-1309, 2019, the authors trained a model in a weakly-supervised framework that did not require pixel-level annotations to classify prostate cancer and validated on ~10,000 whole-slide images sourced from multiple countries. However, some degree of human-in-the-loop curation was performed on their dataset, including manual quality control such as post-hoc removal of slides with pen ink from the study. Pantanowitz, et al, *An artificial intelligence algorithm for prostate cancer diagnosis in whole-slide images of core needle biopsies: a blinded clinical validation and deployment study*, The Lancet Digital Health, 2(8):e407-e416, 2020 describes using pixel-wise annotations to develop a model trained on ~550 whole-slide images that distinguish high-grade from low-grade prostate cancer. In dermatopathology, the model developed in Ianni, et al., *Tailored for real-world: A whole-slide image classification system validated on uncurated multi-site data emulating the prospective pathology workload*, Nature Scientific Reports, 10(1):1-12, 2020, hereinafter, "Ianni 2020", classified skin lesion specimens between four morphology-based groups, was tested on ~13,500 whole-slide images, and also demonstrated that use of confidence thresholding could provide a high accuracy; however, it grouped malignant melanoma with all other benign melanocytic lesions, limiting its potential uses. Additionally, all previous attempts at pathology classification using deep learning have, at their greatest level of abstraction, performed classification at the level of a whole-slide image or a sub-region of a whole-slide image. Because a pathologist is required to review all whole-slide images from a tissue specimen, previous deep learning pathology efforts therefore do not leverage the same visual information that a pathologist would have at hand to perform a diagnosis, require some curation of datasets to ensure that pathology is present in all training slides, and implement ad-hoc rules for combining the predictions of each whole-slide corresponding to a specimen. Most have also neglected the effect of diagnostic discordance on their ground truth, resulting in potentially mislabeled training and testing data.

Thus, this Section presents a reduction to practice that can classify skin cases for triage and prioritization prior to pathologist review. Unlike previous systems, the reduction to practice performs hierarchical melanocytic specimen classification into low (MPATH I-II), Intermediate (MPATH III), or High (MPATH IV-V) diagnostic categories, allowing for prioritization of melanoma cases. The reduction to practice was the first to classify skin biopsies at the specimen level through a collection of whole-slide images that represent the entirety of the tissue from a single specimen, e.g., a supra-image. This training procedure is analogous to the process of a dermatopathologist, who reviews the full collection of scanned whole-slide images corresponding to a specimen to make a diagnosis. Finally, the reduction to practice was trained and validated on the largest dataset of consensus-reviewed melanocytic specimens published to date. The reduction to practice was built to be scalable and ready for the real-world, built without any pixel-level annotations, and incorporating the automatic removal of scanning artifacts.

B. Reference and Validation Lab Data Collection

The reduction to practice was trained using slides from 3511 specimens (consisting of 7685 whole-slide images) collected from a leading dermatopathology lab in a top academic medical center (Department of Dermatology at University of Florida College of Medicine), which is referred to as the "Reference Lab". The Reference Lab dataset consisted of both an uninterrupted series of sequentially-accessioned cases (69% of total specimens) and a targeted set, curated to enrich for rarer melanocytic pathologies (31% of total specimens). Melanocytic specimens were only included in this set if three dermatopathologists' consensus on diagnosis could be established. The whole-slide images consisted exclusively of H&E-stained, formalin-fixed, paraffin-embedded dermatopathology tissue and were scanned using a 3DHistech P250 High Capacity Slide Scanner at an objective power of 20×, corresponding to 0.24 μm/pixel. The final classification given by the reduction to practice was one of six classes, defined by their morphologic characteristics:

1. Basaloid: containing abnormal proliferations of basaloid-oval cells, primarily basal cell carcinoma of various types;
2. Squamous: containing malignant squamoid epithelial proliferations, consisting primarily of squamous cell carcinoma (invasive and in situ);
3. Melanocytic Low Risk: benign to moderately atypical melanocytic nevi/proliferation of cells of melanocytic origin, classified as the MPATH I or MPATH II diagnostic category;
4. Melanocytic Intermediate Risk: severely atypical melanocytic nevi or melanoma in situ, classified as the MPATH III diagnostic category;
5. Melanocytic High Risk: invasive melanoma, classified as the MPATH IV or V diagnostic category; or
6. Other: all skin specimens that do not fit into the above classes, including but not limited to inflammatory conditions and benign proliferations of squamoid epithelial cells.

The overall reference set was composed of 544 Basaloid, 530 Squamous, 1079 Melanocytic and 1358 Other specimens. Of the Melanocytic specimens, 764 were Low Risk, 213 were Intermediate Risk and 102 were High Risk. The heterogeneity of this reference set is illustrated in Table 1, below.

TABLE 1

Counts of each of the general pathologies in the reference set from the Reference Lab, broken-out into specific diagnostic entities

| Diagnostic Morphology | Counts |
| --- | --- |
| Basaloid | 544 |
| Nodular Basal Cell Carcinoma | 404 |
| Basal Cell Carcinoma, NOS | 123 |
| Basal Cell Carcinoma, Morphea type | 7 |
| Pilomatrixoma | 5 |
| Infiltrative Basal Cell Carcinoma | 5 |
| Squamous | 530 |
| Invasive Squamous Cell Carcinoma | 269 |
| Squamous Cell Carcinoma in situ (Bowen's Disease) | 254 |
| Fibrokeratoma | 4 |
| Warty Dyskeratoma | 3 |
| Melanocytic High Risk | 102 |
| Melanoma | 102 |
| Melanocytic Intermediate Risk | 213 |
| Melanoma In Situ | 202 |
| Severe Dysplasia | 9 |
| Melanocytic Low Risk | 764 |
| Conventional Melanocytic Nevus (acquired and congenital) | 368 |
| Mild Dysplasia | 289 |
| Moderate Dysplasia | 75 |
| Halo Nevus | 14 |
| Dysplastic Nevus, NOS | 12 |
| Spitz Nevus | 2 |
| Blue Nevus | 2 |
| Other Diagnoses | 1360 |

The specimen counts presented herein for the melanocytic classes reflect counts following three-way consensus review (see Section IV(C)). For training, validating, and testing the reduction to practice, this dataset was divided into three partitions by sampling at random without replacement with 70% of specimens used for training, and 15% used for each of validation and testing.

To validate performance and generalizability across labs, scanners, and associated histopathology protocols, several large datasets of similar composition to the Reference Lab were collected from leading dermatopathology labs of two additional top academic medical centers (Jefferson Dermatopathology Center, Department of Dermatology Cutaneous Biology, Thomas Jefferson University, denoted as "Validation Lab 1", and Department of Pathology and Laboratory Medicine at Cedars-Sinai Medical Center, which is denoted as "Validation Lab 2"). These datasets are both comprised of: (1) an uninterrupted set of sequentially-accessioned cases—65% for Validation Lab 1, 24% for Validation Lab, and (2) a set targeted to heavily sample melanoma, pathologic entities that mimic melanoma, and other rare melanocytic specimens. Specimens from Validation Lab 1 consisted of slides from 2795 specimens (3033 whole-slide images), scanned using a 3DHistech P250 High Capacity Slide Scanner at an objective power of 20×(0.24 μm/pixel). Specimens from Validation Lab 2 consisted of slides from 2066 specimens (2066 whole-slide images; each specimen represented by a single whole-slide image), with whole-slide images scanned using a Ventana DP 200 scanner at an objective power of 20×(0.47 μm/pixel). Note: specimen and whole-slide image counts above reflect specimens included in the study after screening melanocytic specimens for inter-pathologist consensus. Table 2 shows the class distribution for the Validation labs.

TABLE 2

| Class counts for the Validation Lab datasets | | |
| --- | --- | --- |
| Label Category | Validation Lab 1 | Validation Lab 2 |
| MPATH I-II | 1457 | 458 |
| MPATH III | 225 | 364 |
| MPATH IV-V | 100 | 361 |
| Basaloid | 198 | 265 |
| Squamous | 104 | 55 |
| Other | 711 | 563 |

D. Consensus Review

There are high discordance rates in diagnosing melanocytic specimens. Elmore et al. [4] studied 240 dermatopathology cases and found that the consensus rate for MPATH Class II lesions was 25%, for MPATH Class III lesions 40%, and for MPATH Class IV 45%. Therefore, three board-certified pathologists reviewed each melanocytic specimen to establish a reliable ground truth for melanocytic cases in the implementation of the reduction to practice described herein. The first review was the original specimen diagnosis made via glass slide examination under a microscope. Two additional dermatopathologists independently reviewed and rendered a diagnosis digitally for each melanocytic specimen. The patient's year of birth and gender were provided with each specimen upon review. Melanocytic specimens were considered to have a consensus diagnosis and included in the study if:

1. All three dermatopathologists were in consensus on a diagnostic class for the specimen, or 2. Two of three dermatopathologists were in consensus on a diagnostic class for the specimen, and a fourth and fifth pathologist reviewed the specimen digitally and both agreed with the majority classification.

A diagnosis was rendered in the above fashion for every melanocytic specimen obtained from the Reference Lab and Validation Lab 1. All dysplastic and malignant melanocytic specimens from Validation Lab 2 were reviewed by three dermatopathologists, and only the specimens for which consensus could be established were included in the study. No non-melanocytic specimens were reviewed for concordance due to inherently lower known rates of discordance.

For the specimens obtained from the Reference Lab, consensus was established for 75% of specimens originally diagnosed as MPATH I/II, 66% of those diagnosed as MPATH III, 87% of those diagnosed as MPATH IV/V, and for 74% of the reviewed specimens in total. For specimens obtained from Validation Lab 1, pathologists consensus was established for 84% of specimens originally diagnosed as MPATH I/II specimens, 51% of those diagnosed as MPATH III, 54% of those diagnosed as MPATH IV/V, and for 61% of the reviewed specimens in total.

D. Reduction to Practice System Architecture

Figure 6:
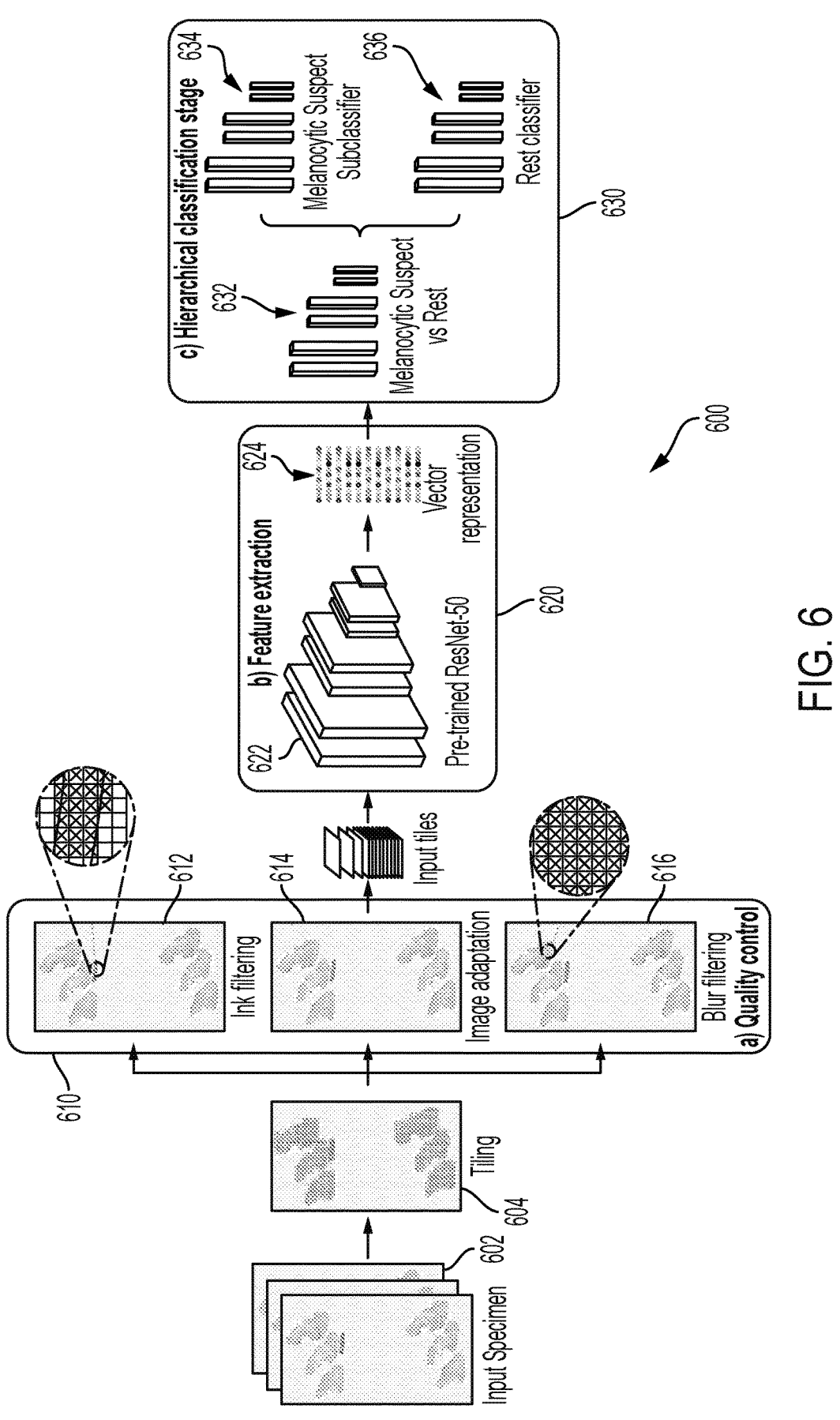
FIG. 6 is a schematic diagram of the system architecture of an example reduction to practice.

FIG. 6 is a schematic diagram of the system architecture 600 of an example reduction to practice. The reduction to practice includes three main components: quality control 610, feature extraction 620, and hierarchical classification 630. A brief description of how the reduction to practice was used to classify a novel supra-image follows. Each specimen 602, a supra-image, was first segmented into tissue-containing regions, subdivided into 128×128 pixel tiles by tiling 604, and extracted at an objective power of 10×. Each tile was passed through the quality control 610, which includes ink filtering 612, blur filtering 616, and image adaptation 614. The image-adapted tiles were then passed through the feature extraction 620 stage, including a pretrained ResNet50 network 622, to obtain embedded vectors 624 as components corresponding to the tiles. Next, the embedded vectors 624 were propagated through the hierarchical classification 630 stage, including an upstream neural network 632 performing a binary classification between "Melanocytic Suspect" and "Rest". Specimens that were classified as "Melanocytic Suspect" were fed into a first downstream neural network 634, which classified between "Melanocytic High Risk, Melanocytic Intermediate Risk" and "Rest". The remaining specimens were fed into a second downstream "Rest" neural network 636, which classified between "Basaloid, Squamous, Melanocytic Low Risk" and "Other". This classification process of the reduction to practice is described in detail presently.

Quality control 610 included ink filtering 612, blur filtering 616, and image adaptation 614. Pen ink is common in labs migrating their workload from glass slides to whole-slide images where the location of possible malignancy was marked. This pen ink represented a biased distractor signal in training the reduction to practice that is highly correlated with malignant or High Risk pathologies. Tiles containing pen ink were identified by a weakly supervised neural network trained to detect inked slides. These tiles were removed from the training and validation data and before inference on the test set. Areas of the image that were out of focus due to scanning errors were also removed to the extent possible by blur filtering 616 by setting a threshold on the variance of the Laplacian over each tile. In order to avoid domain shift between the colors of the training data and validation data, the reduction to practice adopted as its image adaptation 614 the image adaptation procedure in Ianni 2020.

The next component of the reduction to practice, feature extraction 620, extracted informative features from the quality controlled, color-standardized tiles. To capture higher-level features in these tiles, they were propagated through a neural network (ResNet50; He, et al., *Deep residual learning for image recognition*, arXiv preprint arXiv:1512.03385, 2015) trained on the ImageNet (Deng, et al., *Imagenet: A large-scale hierarchical image database*, In IEEE Conference on Computer Vision and Pattern Recognition, pages 248-255, 2009) dataset to embed each input tile into 1024 channel vectors which were then used in subsequent neural networks.

The hierarchical neural network architecture was developed in order to classify both Melanocytic High and Intermediate Risk specimens with high sensitivity. First, the upstream neural network 632 performed a binary classification between "Melanocytic Suspect" (defined as "High or Intermediate Risk") and "Basaloid, Squamous, Low Risk", or "Other" (which are collectively defined as the "Rest" class). Specimens that were classified as "Melanocytic Suspect" were fed into the downstream neural network 634, which further classified the specimen between "Melanocytic High Risk, Melanocytic Intermediate Risk" and "Rest". The remaining specimens, classified as "Rest", were fed into a separate downstream neural network 636, which further classified the specimen between "Basaloid, Squamous, Melanocytic Low Risk" and "Other". Each neural network 632, 634, 636 included four fully-connected layers (two layers of 1024 channels each, followed by two of 512 channels each). Each neuron in the three layers after the input layer was ReLU activated.

The three neural networks 632, 634, 636 in the hierarchy were trained under a weakly-supervised multiple-instance learning (MIL) paradigm. Each embedded tile was treated as an instance of a bag containing all quality-assured tiles of a specimen. Embedded tiles were aggregated using sigmoid-activated attention heads. To help prevent over-fitting, the training dataset included augmented versions of the tiles. Augmentations were generated with the following augmentation strategies: random variations in brightness, hue, contrast, saturation, (up to a maximum of 15%), Gaussian noise with 0.001 variance, and random 90° image rotations. The upstream binary "Melanocytic Suspect vs. Rest" classification neural network 632 and the downstream "Rest" subclassifier neural network 636 were each trained end-to-end with cross-entropy loss. The "Melanocytic Suspect" subclassifier neural network 634 was also trained with cross-entropy loss, but with a multi-task learning strategy. This subclassifier neural network 634 was presented with three tasks: differentiating "Melanocytic High Risk" from "Melanocytic Intermediate Risk" specimens, "Melanocytic High Risk" from "Rest" specimens, and "Melanocytic Intermediate Risk" from "Rest" specimens. The training loss for this subclassifier neural network 634 was computed for each task, but was masked if it did not relate to the ground truth label of the specimen. Two out of three tasks were trained for any given specimen in a training batch. By training in this manner, the shared network layers were used as a generic representation of melanocytic pathologies, while the task branches learned to attend to specific differences to accomplish their tasks.

Figure 7:
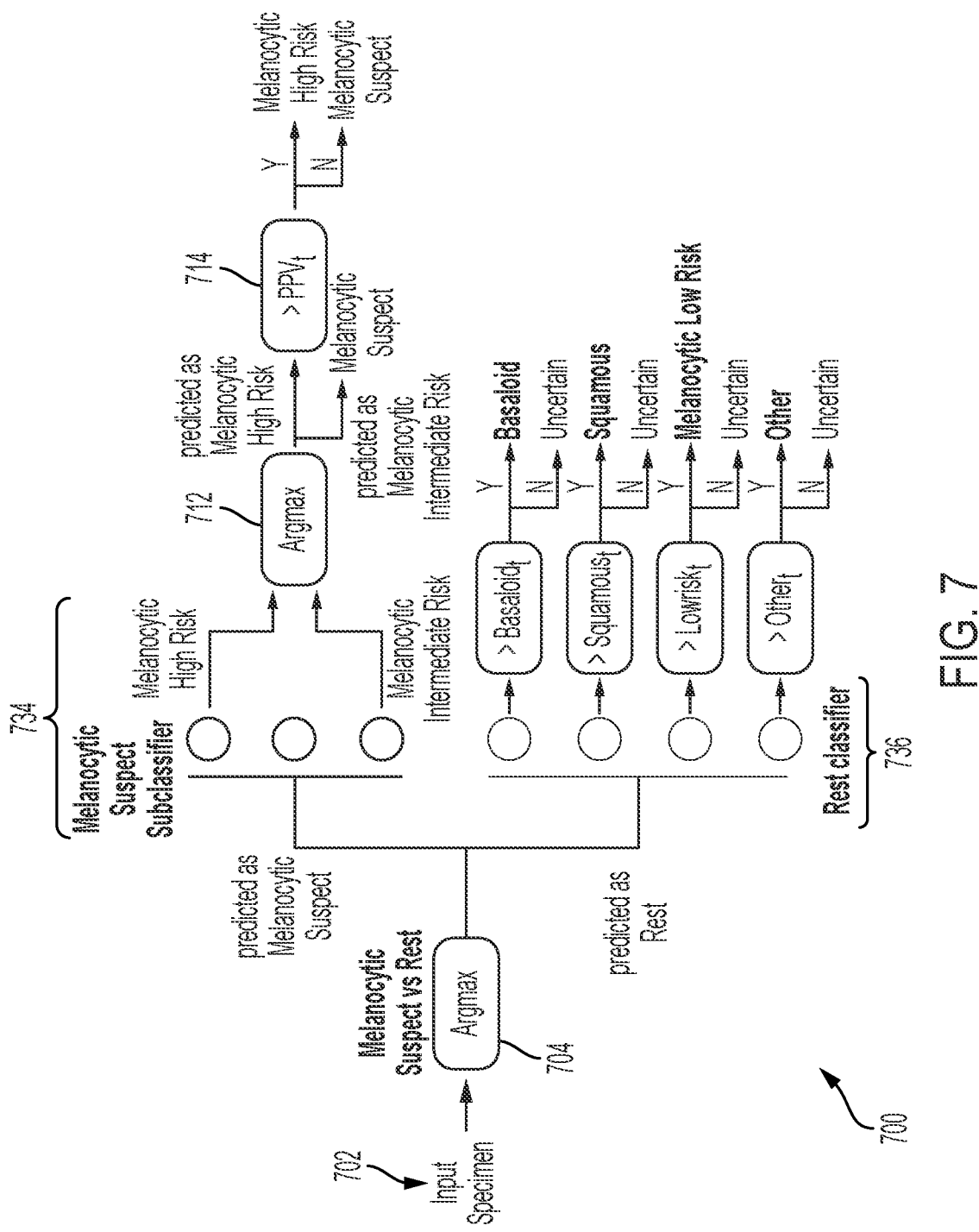
FIG. 7 is a schematic diagram representing a hierarchical classification technique implemented by the reduction to practice of FIG. 6.

FIG. 7 is a schematic diagram representing a hierarchical classification technique 700 implemented by the reduction to practice of FIG. 6. For example, the hierarchal classification technique 700 may be implemented by hierarchal classification 630 as shown and described above in reference to FIG. 6. Thus, FIG. 7 depicts Melanocytic Suspect Subclassifier 734, corresponding to the first downstream neural network 634 of FIG. 6, and depicts Rest subclassifier 736, corresponding to the second downstream neural network 636 of FIG. 6. During inference, the predicted classes of an input specimen 702 (e.g., a supra-image) were computed as follows:

1. The larger of the two confidence values 704 (see below for the confidence thresholding procedure) output from the upstream classifier determined which downstream classifier a specimen was passed to.

2. If the specimen was handed to the "Rest" subclassifier 736, used the highest confidence class probability was used as the predicted label.

3. If the specimen was handed to the Melanocytic Suspect subclassifier 734, the highest confidence class probability between the "Melanocytic High Risk vs Rest" and "Melanocytic Intermediate Risk vs Rest" tasks was used as the predicted label.

As an additional step in the classification pipeline, the hierarchical classification technique 700 performed classification with uncertainty quantification to establish a confidence score for each prediction using a Monte Carlo dropout method following a similar procedure as used by Gal et al., *Dropout as a Bayesian approximation: Representing model uncertainty in deep learning*, In International Conference on Machine Learning, pages 1050-1059, 2016. Using the confidence distribution of the specimens in the validation set of the Reference Lab, the hierarchal classification technique 700 computed confidence threshold values for each predicted class following the procedure outlined in Ianni 2020 by requiring classifications to meet a predefined a level of accuracy in the validation set. Specimens that were predicted as "Melanocytic High Risk" had to pass two confidence thresholds: an accuracy threshold 712 and a PPV threshold 714—both established a priori on the validation set to be predicted as "Melanocytic High Risk"—in order to be predicted as "Melanocytic High Risk". Specimens that were predicted to be "Melanocytic High Risk" but failed to meet these thresholds were predicted as "Melanocytic Suspect". Thresholds that maximized the sensitivity of the reduction to practice to the "Melanocytic Suspect" class were set, while simultaneously maximizing the PPV to the "Melanocytic High Risk" class.

To evaluate how the reduction to practice generalizes to data from other labs, the neural network trained on data from the Reference Lab to both Validation Lab 1 and Validation Lab 2 was fine tuned. A quantity of 255 specimens were set aside from each validation lab (using an equal class distribution of specimens) as the calibration set, of which 210 specimens were used as the training set, and 45 specimens were used as the validation set for fine tuning the neural networks. (The remaining specimens in the validation lab used as the test set.) The final validation lab metrics presented below are reported on the test set with these calibrated neural networks.

E. Performance Evaluation

Figure 8:
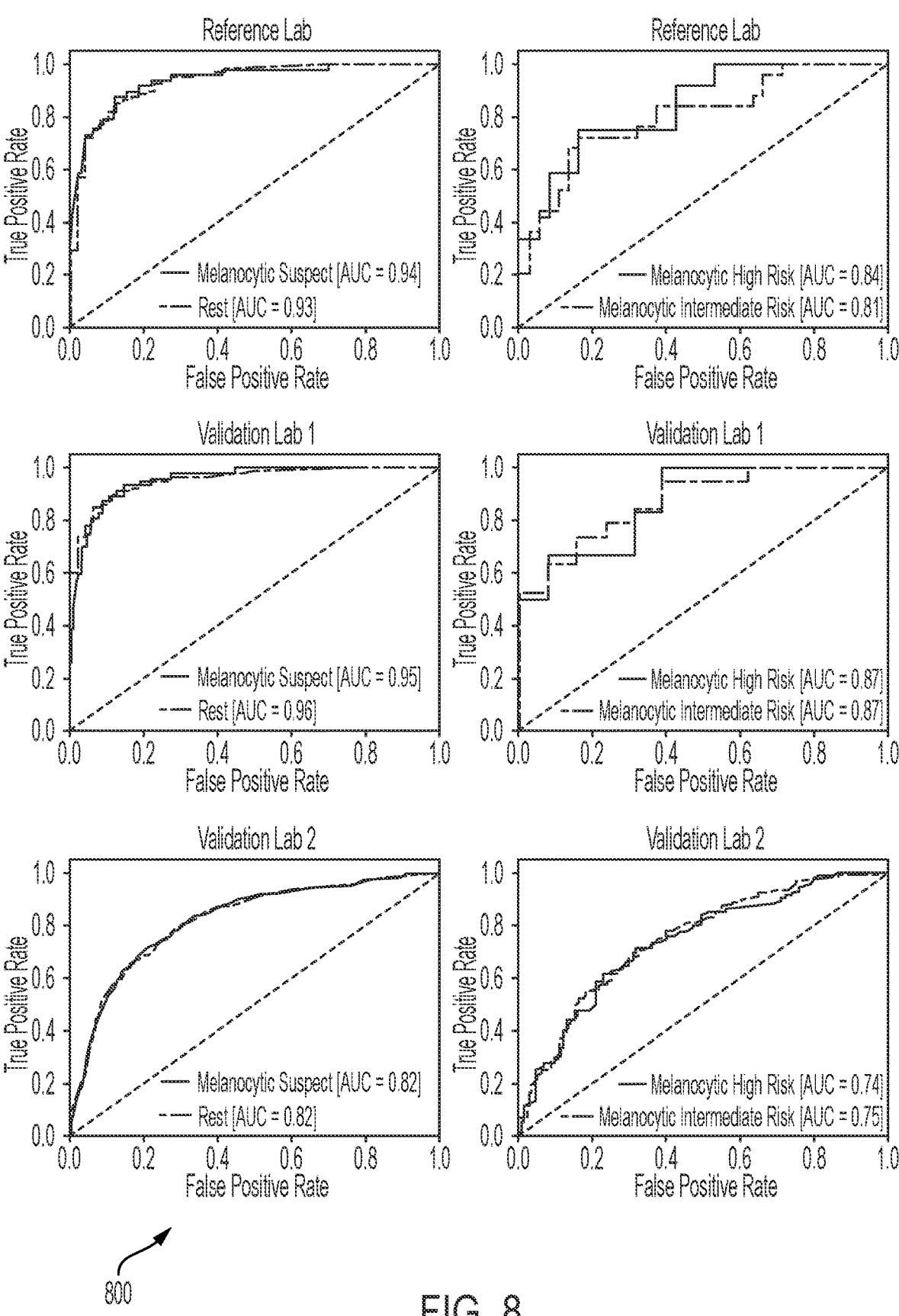
FIG. 8 depicts receiver operating characteristic curves for the neural networks implemented by the reduction to practice of FIG. 6.
Figure 8:
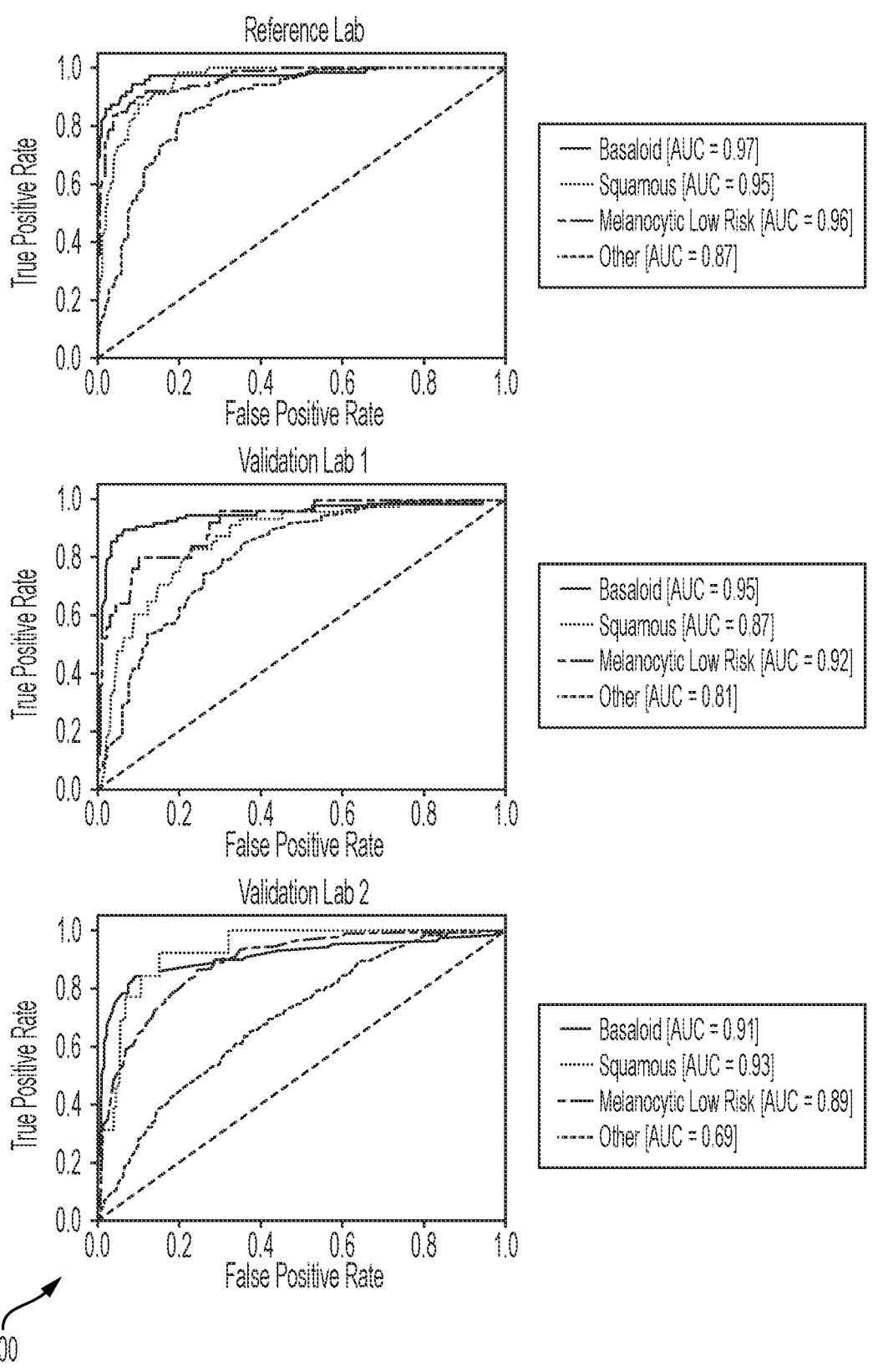

FIG. 8 depicts Receiver Operating Characteristic ("ROC") curves 800 for the neural networks implemented by the reduction to practice of FIG. 6. In particular, the ROC curves derived from the Reference Lab test dataset for the hierarchal neural networks 632, 634, 636 of the reduction to practice as shown and described in reference to FIG. 6 are depicted in FIG. 8. FIG. 8 depicts such results for the upstream classifier (left column), the High & Melanocytic Intermediate classifier (middle column), and the Basaloid, Squamous, Low Risk Melanocytic & Rest classifier (right column), for the Reference Lab (first row), for Validation Lab 1, (second row), and for Validation Lab 2 (third row).

The Area Underneath the ROC Curve ("AUC") values, calculated with the one-vs-rest scoring scheme, were 0.97, 0.95, 0.87, 0.84, 0.81, 0.93, and 0.96 for the Basaloid, Squamous, Other, Melanocytic High Risk, Melanocytic Intermediate Risk, Melanocytic Suspect, and Melanocytic Low Risk classes, respectively. Table 3 shows the performance of the reduction to practice with respect to diagnostic entities of clinical interest on the Reference Lab test dataset. In particular, Table 3 shows metrics for selected diagnoses of clinical interest, based on the reference Lab test set, representing the classification performance of the individual diagnoses into their higher-level classes: e.g., a correct classification of "Melanoma" is the prediction "Melanocytic High Risk". Results are class-weighted according to the relative prevalence in the test set.

TABLE 3

Metrics for selected diagnoses of clinical interest

| Diagnosis | PPV | Sensitivity | F1 Score | Balanced Accuracy | Support |
|---|---|---|---|---|---|
| Melanoma → Melanocytic High Risk | 0.66 | 0.45 | 0.47 | 0.52 | 23 |
| Melanoma → Melanocytic Suspect | 1.00 | 0.83 | 0.90 | 0.83 | 23 |
| Melanoma in situ → Melanocytic Intermediate Risk | 1.00 | 0.75 | 0.86 | 0.75 | 20 |
| Melanoma in situ → Melanocytic Suspect | 1.00 | 0.85 | 0.92 | 0.85 | 20 |
| Spitz Nevus | 0.00 | 0.00 | 0.00 | 0.00 | 2 |
| Dysplastic Nevus | 0.91 | 0.76 | 0.82 | 0.56 | 61 |
| Dermal Nevus | 1.00 | 0.81 | 0.90 | 0.81 | 28 |
| Compound Nevus | 0.94 | 0.75 | 0.82 | 0.55 | 73 |
| Junctional Nevus | 0.84 | 0.77 | 0.80 | 0.42 | 61 |
| Halo Nevus | 1.00 | 1.00 | 1.00 | 1.00 | 20 |
| Blue Nevus | 1.00 | 0.67 | 0.80 | 0.67 | 68 |
| Squamous Cell Carcinoma | 1.00 | 0.81 | 0.89 | 0.81 | 15 |
| Bowen's Disease | 1.00 | 0.85 | 0.92 | 0.85 | 4 |
| Basal Cell Carcinoma | 1.00 | 0.84 | 0.91 | 0.84 | 8 |

The sensitivity of the reduction to practice to the Melanocytic Suspect class was found to be 0.83, 0.85 for the Melanocytic High and Intermediate risk classes, respectively. The PPV to Melanocytic High Risk was found to be 0.57. The dropout Monte Carlo procedure set the threshold for Melanocytic High Risk classification very high; specimens below this threshold were classified as Melanocytic Suspect, maximizing the sensitivity to this class.

After fine-tuning all three neural networks in the hierarchy through the calibration procedure in each validation lab, the reduction to practice was able to generalize to unseen data from both validation labs as depicted in FIG. 8. Note that fine-tuning was not performed for any of the neural networks in the pre-processing pipeline (Colorization, Ink Detection or ResNet). The ROC curves derived from the Validation Lab 1 and Validation Lab 2 test datasets are shown in FIG. 8. The AUC values for Validation Lab 1 were 0.95, 0.88, 0.81, 0.87, 0.87, 0.95, and 0.92 for the Basaloid, Squamous, Other, Melanocytic High Risk, Intermediate Risk, Suspect, and Low Risk classes, respectively and the AUC values for the same classes for Validation Lab 2 were 0.93, 0.92, 0.69, 0.76, 0.75, 0.82, and 0.92.

F. Consensus Ablation Study

Figure 9:
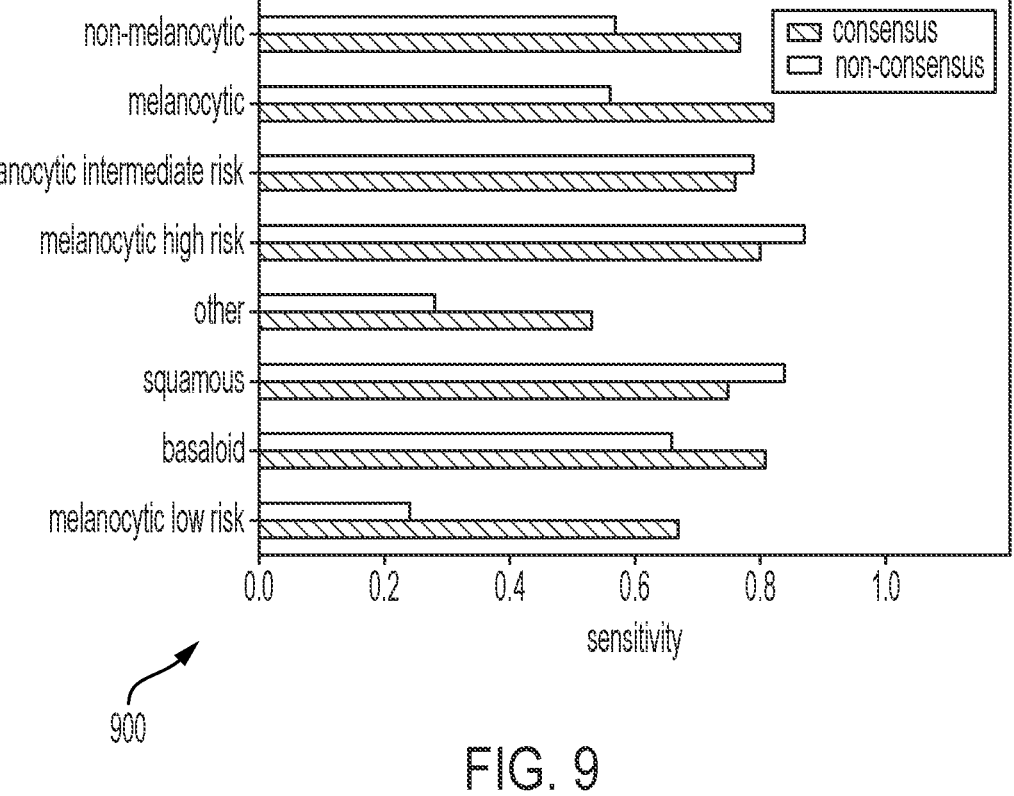
FIG. 9 depicts a chart comparing reference lab performance on the same test set when trained on consensus and non-consensus data.

FIG. 9 depicts a chart 900 comparing reference lab performance on the same test set when trained on consensus and non-consensus data. The melanocytic class referenced in chart 900 is defined as the Low, Intermediate and High Risk classes. The sensitivity of the Melanocytic Intermediate and High Risk classes are defined with respect to the reduction to practice classifying these classes as suspect. The PPV to melanocytic high risk in the non-consensus trained model was 0.33, while the consensus model was 0.57.

In general, diagnosing melanocytic cases is challenging. Although some specimens (such as ones diagnosed as compound nevi) clearly exhibit very low risk, and others (such as invasive melanoma) exhibit very high risk of progressing into life threatening conditions, reproducible stratification in the middle of the morphological spectrum has historically proved difficult. The results disclosed in this Section were derived with the reduction to practice trained and evaluated on consensus data: data for which the ground truth melanocytic specimen diagnostic categories were agreed upon by multiple experts. To understand the effect of consensus on training deep learning neural networks, an ablation study was performed by training two hierarchical neural networks. Both neural networks used all non-melanocytic specimens available in the training set. The first neural network was trained only including melanocytic specimens for which consensus was obtained under the diagnostic categories of MPATH I/II, MPATH III, or MPATH IV/V. The other neural network was trained by also including non-consensus data: melanocytic specimens whose diagnostic category was not agreed upon by the experts. To facilitate a fair comparison, validation sets for both neural network versions and a common consensus test set derived from the Reference Lab were reserved. The sensitivities of the reduction to practice to different classes on both consensus and non-consensus data are shown in FIG. 9, where a clear improvement is shown in the sensitivity to the Melanocytic class of over 40% for melanocytic specimens that are annotated with consensus labels over ones that are not; this primarily manifested from a reduction in false positive Melanocytic Suspect classifications.

G. Discussion

This document discloses a reduction to practice capable of automatically sorting and triaging skin specimens with high sensitivity to Melanocytic Suspect cases prior to review by a pathologist. By contrast, prior art techniques may provide diagnostically-relevant information on a potential melanoma specimen only after a pathologist has reviewed the specimen and classified it as a Melanocytic Suspect lesion.

The ability of the reduction to practice to classify suspected melanoma prior to pathologist review could substantially reduce diagnostic turnaround time for melanoma by not only allowing timely review and expediting the ordering of additional tests or stains, but also ensuring that suspected melanoma cases are routed directly to subspecialists. The potential clinical impact of an embodiment with these capabilities is underscored by the fact that early melanoma detection is correlated with improved patient outcomes.

Figure 10:
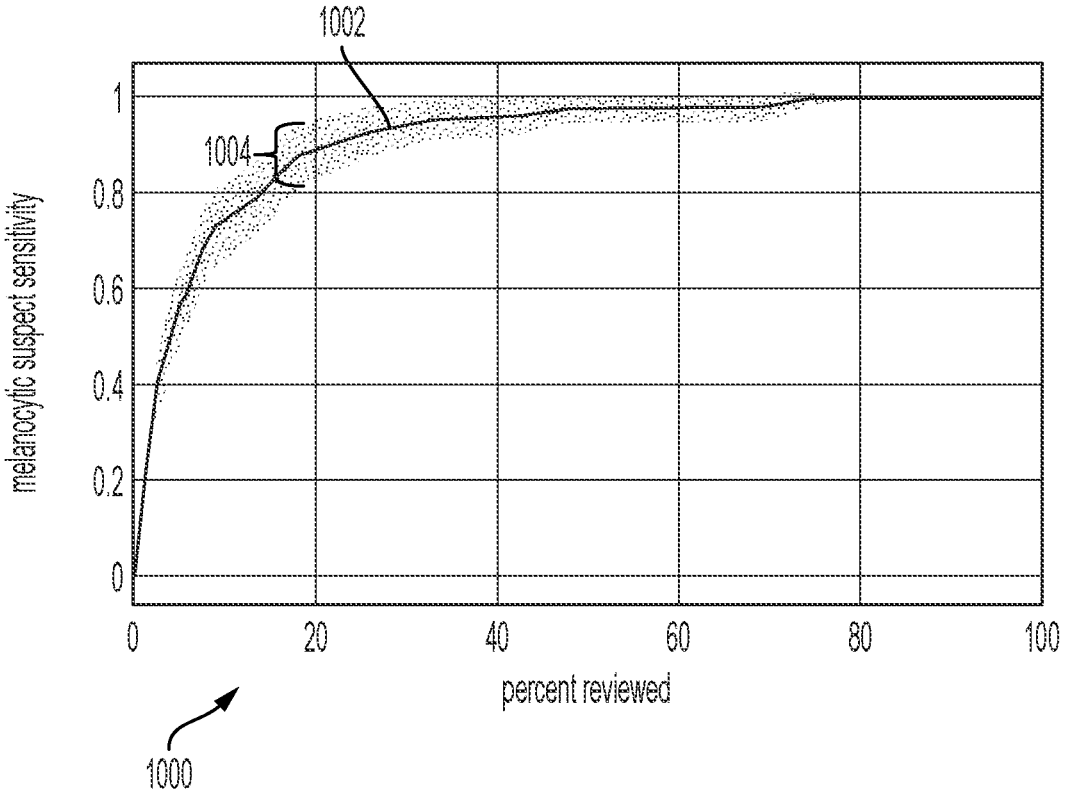
FIG. 10 depicts a chart depicting mean and standard deviation sensitivity to melanoma versus percentage reviewed for 1,000 simulated sequentially accessioned datasets, drawn from reference lab confidence scores.

FIG. 10 depicts a chart 1000 depicting mean and standard deviation sensitivity to melanoma versus percentage reviewed for 1,000 simulated sequentially accessioned datasets, drawn from reference lab confidence scores. In particular, chart 1000 depicts mean 1002 and standard deviation sensitivity 1002 to melanoma versus percentage reviewed for 1,000 simulated sequentially-accessioned datasets, drawn from Reference Lab confidence scores. In the clinic, 95% of melanoma suspect cases are detected within the first 30% of cases, when ordered by melanoma suspect model confidence.

As the reduction to practice was optimized to maximize melanoma sensitivity, the performance was investigated as a simple Melanocytic Suspect binary classifier. The reduction to practice may be used to sort a pathologist's work list of specimens by the reduction to practice's confidence (in descending order) in the upstream classifier's suspect melanocytic classification. FIG. 10 demonstrates the resulting sensitivity to the Melanocytic Suspect class against the percentage of total specimens that a pathologist would have to review in this sorting scheme in order to achieve that sensitivity. A pathologist would only need between 30% and 60% of the caseload to address all melanoma specimens according to this dataset.

Diagnostic classification of melanocytic lesions remains challenging. There is known lack of consensus among pathologists, and a disturbing lack of intra-pathologist concordance over time was recently reported. Training with consensus data resulted in improved performance seen in classifications excluding Melanocytic Suspect, which has the highest pathologist discordance rates, as show in in Chart 1000. Because pathologists tend to cautiously diagnose a benign lesion as malignant, the reduction to practice learned the same bias in absence of consensus. By training on consensus of multiple dermatopathologists, the reduction to practice may have the unique ability to learn a more consistent feature representation of melanoma and aid in flagging misdiagnosis. While the reduction to practice is highly sensitive to melanoma (84% correctly detected as Intermediate or High Risk in the Reference Lab Test set) there are a large number of false positives (2.7% of sequentially-accessioned specimens in the reference lab were predicted to be suspect) classified as suspect. It may therefore be possible to flag initial diagnoses discordant with the reduction to practice's classification of highly confident predictions for review in order to lower the false positive rate.

The reduction to practice also enables other automated pathology workflows in addition to triage and prioritization of suspected melanoma cases. Sorting and triaging specimens into other classifications such as Basaloid could allow the majority of less complicated cases (such as basal cell carcinoma) to be directly assigned to general pathologists, or to dermatologists who routinely sign out such cases. Relevant to any system designed for clinical use is how well its performance generalizes to sites on which the system was not trained. Performance of the reduction to practice on the Validation Labs after calibration (as shown in FIG. 10) was in many cases close to that of the Reference Lab.

Some further aspects are defined in the following clauses:

Clause 1: A computer-implemented method of determining a presence of a pathology property in a supra-image, the method comprising: receiving an electronic evaluation supra-image; providing the electronic evaluation supra-image to an electronic neural network that has been trained, using a training corpus of training supra-images and on an electronic computer, to determine the presence of the pathology property in a supra-image, each training supra-image comprising at least one image, each image corresponding to a plurality of components, wherein each training supra-image of the training corpus is associated with a respective electronic label indicating whether the pathology property is present, wherein the training corpus is sufficient to train the electronic neural network to determine a presence of the pathology property; receiving from the electronic neural network an output indicative of whether the pathology property is present in the evaluation supra-image; and providing the output.

Clause 2: The method of Clause 1, wherein the electronic computer comprises volatile electronic memory having a storage capacity, wherein a probability that the pathology property is present in at least one component of a sampled collection of components of images of at least one training supra-image of the training corpus indicates that the training corpus is sufficient to train the electronic neural network to determine the presence of the pathology property, wherein the storage capacity of the volatile electronic memory is sufficient to store the sampled collection of components simultaneously.

Clause 3: The method of Clause 1 or Clause 2, further comprising: obtaining, for each respective component of each image of the at least one training supra-image of the training corpus, a respective electronic label indicating whether the pathology property is present in the respective component, whereby a plurality of labels is obtained; wherein the probability is based on at least the plurality of labels.

Clause 4: The method of any of Clauses 1-3, further comprising: calculating, based on at least the plurality of labels, the probability; and determining, based on at least the probability, that the training corpus is sufficient to train the electronic neural network to determine the presence of the pathology property.

Clause 5: The method of any of Clauses 1-4, wherein the probability comprises $$1 - \frac{n_{neg}! \, (N - n_{RAM})!}{N! \, (n_{neg} - n_{RAM})!},$$

wherein N represents a number of components of the sampled collection of components, $n_{neg}$ represents a number of components of the sampled collection of components that lack the pathology property, and $n_{RAM}$ represents a maximum number of components that can be simultaneously stored in the volatile electronic memory.

Clause 6: The method of any of Clauses 1-5, wherein the electronic neural network has been trained, using the training corpus of training supra-images and on an electronic computer, to determine the presence of the pathology property in a supra-image by: randomly sampling collections of components corresponding to images from individual training supra-images, whereby a plurality of collections of components are obtained; labeling the collections of components according to a respective electronic label for their respective supra-image, whereby a plurality of weakly labeled collections of components are obtained from the plurality of collections of components; iteratively training, through the plurality of weakly labeled collections of components, the electronic neural network to determine the presence of the pathology property.

Clause 7: The method of any of Clauses 1-6, wherein the evaluation supra-image and a plurality of the training supra-images represent biopsies.

Clause 8: The method of any of Clauses 1-7, wherein each image of a plurality of the training supra-images comprises a whole-slide image, wherein the evaluation supra-image comprises at least one whole-slide image.

Clause 9: The method of any of Clauses 1-8, wherein each component comprises a feature vector.

Clause 10: The method of any of Clauses 1-9, wherein the pathology property comprises one of: a presence of a malignancy, a presence of a specific grade of malignancy, or a presence of a category of risk.

Clause 11: The method of any of Clauses 2-10 wherein the probability is greater than 0.5.

Clause 12: The method of any of Clauses 2-11 wherein the probability is greater than 0.9.

Clause 13: The method of any of Clauses 2-12 wherein the probability is greater than 0.95.

Clause 14: The method of any of Clauses 1-13, wherein the electronic volatile memory comprises Random Access Memory (RAM).

Clause 15: The method of any of Clauses 1-14, wherein the RAM comprises a portion of at least one Graphical Processing Unit (GPU).

Clause 16: A system for determining a presence of a pathology property in a supra-image, the system comprising: a processor; and a memory communicatively coupled to the processor, the memory storing instructions which, when executed on the processor, perform operations comprising: receiving an electronic evaluation supra-image; providing the electronic evaluation supra-image to an electronic neural network that has been trained, using a training corpus of training supra-images and on an electronic computer, to determine the presence of the pathology property in a supra-image, each training supra-image comprising at least one image, each image corresponding to a plurality of components, wherein each training supra-image of the training corpus is associated with a respective electronic label indicating whether the pathology property is present, wherein the training corpus is sufficient to train the electronic neural network to determine a presence of the pathology property; receiving from the electronic neural network an output indicative of whether the pathology property is present in the evaluation supra-image; and providing the output.

Clause 17: The system of Clause 16, wherein the electronic computer comprises volatile electronic memory having a storage capacity, wherein a probability that the pathology property is present in at least one component of a sampled collection of components of images of at least one training supra-image of the training corpus indicates that the training corpus is sufficient to train the electronic neural network to determine the presence of the pathology property, wherein the storage capacity of the volatile electronic memory is sufficient to store the sampled collection of components simultaneously.

Clause 18: The system of Clause 16 or Clause 17, wherein the operations further comprise: obtaining, for each respective component of each image of the at least one training supra-image of the training corpus, a respective electronic label indicating whether the pathology property is present in the respective component, whereby a plurality of labels is obtained; wherein the probability is based on at least the plurality of labels.

Clause 19: The system of any of Clauses 16-18, wherein the operations further comprise: calculating, based on at least the plurality of labels, the probability; and determining, based on at least the probability, that the training corpus is sufficient to train the electronic neural network to determine the presence of the pathology property.

Clause 20: The system of any of Clauses 16-19, wherein the probability comprises $$1 - \frac{n_{neg}! \, (N - n_{RAM})!}{N! \, (n_{neg} - n_{RAM})!},$$

wherein N represents a number of components of the sampled collection of components, $n_{neg}$ represents a number of components of the sampled collection of components that lack the pathology property, and $n_{RAM}$ represents a maximum number of components that can be simultaneously stored in the volatile electronic memory.

Clause 21: The system of any of Clauses 16-20, wherein the electronic neural network has been trained, using the training corpus of training supra-images and on an electronic computer, to determine the presence of the pathology property in a supra-image by: randomly sampling collections of components corresponding to images from individual training supra-images, whereby a plurality of collections of components are obtained; labeling the collections of components according to a respective electronic label for their respective supra-image, whereby a plurality of weakly labeled collections of components are obtained from the plurality of collections of components; iteratively training, through the plurality of weakly labeled collections of components, the electronic neural network to determine the presence of the pathology property.

Clause 22: The system of any of Clauses 16-21, wherein the evaluation supra-image and a plurality of the training supra-images represent biopsies.

Clause 23: The system of any of Clauses 16-22, wherein each image of a plurality of the training supra-images comprises a whole-slide image, wherein the evaluation supra-image comprises at least one whole-slide image.

Clause 24: The system of any of Clauses 16-23, wherein each component comprises a feature vector.

Clause 25: The system of any of Clauses 16-24, wherein the pathology property comprises one of: a presence of a malignancy, a presence of a specific grade of malignancy, or a presence of a category of risk.

Clause 26: The system of any of Clauses 17-25 wherein the probability is greater than 0.5.

Clause 27: The system of any of Clauses 17-26 wherein the probability is greater than 0.9.

Clause 28: The system of any of Clauses 17-27 wherein the probability is greater than 0.95.

Clause 29: The system of any of Clauses 17-28, wherein the electronic volatile memory comprises Random Access Memory (RAM).

Clause 30: The system of Clause 29, wherein the RAM comprises a portion of at least one Graphical Processing Unit (GPU).

Clause 31: A method of training, using an electronic computer, an electronic neural network to determine a presence of a pathology property in a supra-image, the method comprising: accessing a training corpus of electronically stored training supra-images, each training supra-image comprising at least one image, each image corresponding to a plurality of components, wherein each respective training supra-image is associated with a respective electronic label indicating whether the pathology property is present in the respective training supra-image, wherein the training corpus is sufficient for training the electronic neural network to identify the pathology property; and training, using the electronic computer, the training corpus of training supra-images, and the respective electronic labels, the electronic neural network to determine the presence of the pathology property, whereby a trained electronic neural network is obtained.

Clause 32: The method of Clause 31, wherein the electronic computer comprises volatile electronic memory having a storage capacity, wherein a probability that the pathology property is present in at least one component of a subsampled collection of components of images of at least one training supra-image of the training corpus indicates that the training corpus is sufficient for use as the training corpus of supra-images for training the electronic neural network to identify the pathology property, wherein the storage capacity of the volatile electronic memory is sufficient to store the subsampled collection of components simultaneously.

Clause 33: The method of Clause 31 or Clause 32, further comprising: obtaining, for each respective component of each image of the at least one training supra-image, a respective electronic sub-label indicating whether the pathology property is present in the respective component, whereby a plurality of sub-labels are obtained; wherein the probability is based on at least the plurality of sub-labels.

Clause 34: The method of any of Clauses 31-33, further comprising: calculating, based on at least the plurality of sub-labels, the probability; and determining, based on at least the probability, that the training corpus of supra-images is sufficient for training the electronic neural network to identify the pathology property.

Clause 35: The method of any of Clauses 31-34, wherein the probability comprises $$p = 1 - \frac{n_{neg}! \, (N - n_{RAM})!}{N! \, (n_{neg} - n_{RAM})!},$$

wherein p represents the probability, N represents a total number of components of the subsampled collection of components, $n_{neg}$ represents a number of components of the subsampled collection of components that lack the pathology property, and n RAM represents a maximum number of components that can be simultaneously stored in the volatile electronic memory.

Clause 36: The method of any of Clauses 32-35, wherein the probability is greater than 0.5.

Clause 37: The method of any of Clauses 32-36, wherein the probability is greater than 0.9.

Clause 38: The method of any of Clauses 32-37, wherein the probability is greater than 0.95.

Clause 39: The method of any of Clauses 32-38, wherein the electronic volatile memory comprises Random Access Memory (RAM).

Clause 40: The method of Clause 39, wherein the RAM comprises a portion of at least one Graphical Processing Unit (GPU).

Clause 41: The method of any of Clauses 31-40, wherein the training comprises: randomly sampling collections of components corresponding to images from individual training supra-images of the training corpus, whereby a plurality of collections of components are obtained; labeling the collections of components according to a respective electronic label for their respective supra-image, whereby a plurality of weakly labeled collections of components are obtained from the plurality of collections of components; iteratively training, through the plurality of weakly labeled collections of components, the electronic neural network to determine the presence of the pathology property.

Clause 42: The method of any of Clauses 31-41, further comprising: applying the trained neural network to an evaluation supra-image; and obtaining an evaluation from the trained neural network, wherein the evaluation indicated whether the pathology property is present in the evaluation supra-image.

Clause 43: The method of any of Clauses 31-42, wherein each supra-image represents a biopsy.

Clause 44: The method of any of Clauses 31-43, wherein each image comprises a whole-slide image.

Clause 45: The method of any of Clauses 31-44, wherein each component comprises a 128-pixel-by-128-pixel square.

Clause 46: The method of any of Clauses 31-45, wherein each component comprises a feature vector.

Clause 47: The method of any of Clauses 31-46, wherein the pathology property comprises one of: a presence of a malignancy, a presence of a specific grade of malignancy, or a presence of a category of risk.

Clause 48: Computer readable storage comprising a representation of an electronic neural network of any of Clauses 1-47.

Clause 49: An electronic computer comprising at least one electronic processor communicatively coupled to electronic persistent memory comprising instructions that, when executed by the at least one processor, configure the at least one processor to perform operations of any of Clauses 1-48.

Clause 50: At least one non-transitory computer-readable medium comprising computer-readable instructions which, when executed by at least one electronic processor, configure the at least one electronic processor to perform operations of any of Clauses 1-49.

Certain embodiments can be performed using a computer program or set of programs. The computer programs can exist in a variety of forms both active and inactive. For example, the computer programs can exist as software program(s) comprised of program instructions in source code, object code, executable code or other formats; firmware program(s), or hardware description language (HDL) files. Any of the above can be embodied on a transitory or non-transitory computer readable medium, which include storage devices and signals, in compressed or uncompressed form. Exemplary computer readable storage devices include conventional computer system RAM (random access memory), ROM (read-only memory), EPROM (erasable, programmable ROM), EEPROM (electrically erasable, programmable ROM), and magnetic or optical disks or tapes.

While the invention has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

Note that any of the following claims may be combined with any other of the following claims to the extent that antecedent bases for terms in such are clear.

What is claimed is:

1. A computer-implemented method of determining a presence of a pathology property in a supra-image, the method comprising:

receiving an electronic evaluation supra-image, wherein the electronic evaluation supra-image comprises constituent images of a same specimen;

providing the electronic evaluation supra-image to an electronic neural network that has been trained, using a training corpus of training supra-images and on an electronic computer, to determine the presence of the pathology property in a supra-image, each training supra-image comprising at least one image of a same specimen, each image corresponding to a plurality of components, wherein a respective component comprises a tile of an image or a feature vector representative of the tile, wherein each training supra-image of the training corpus is associated with a respective electronic label indicating whether the pathology property is present, wherein the training corpus is sufficient to train the electronic neural network to determine a presence of the pathology property;

receiving from the electronic neural network an output indicative of whether the pathology property is present in the evaluation supra-image; and providing the output.

2. The method of claim 1, wherein the electronic computer comprises volatile electronic memory having a storage capacity, wherein a probability that the pathology property is present in at least one component of a sampled collection of components of images of at least one training supra-image of the training corpus indicates that the training corpus is sufficient to train the electronic neural network to determine the presence of the pathology property, wherein the storage capacity of the volatile electronic memory is sufficient to store the sampled collection of components simultaneously.

3. The method of claim 2, further comprising:

obtaining, for each respective component of each image of the at least one training supra-image of the training corpus, a respective electronic label indicating whether the pathology property is present in the respective component, whereby a plurality of labels is obtained;

wherein the probability is based on at least the plurality of labels.

4. The method of claim 3, further comprising:

calculating, based on at least the plurality of labels, the probability; and determining, based on at least the probability, that the training corpus is sufficient to train the electronic neural network to determine the presence of the pathology property.

5. The method of claim 2, wherein the probability comprises:

$$1 - \frac{n_{neg}! \, (N - n_{RAM})!}{N! \, (n_{neg} - n_{RAM})!}$$

wherein N represents a number of components of the sampled collection of components, $n_{neg}$ represents a number of components of the sampled collection of components that lack the pathology property, and $n_{RAM}$ represents a maximum number of components that can be simultaneously stored in the volatile electronic memory.

6. The method of claim 1, wherein the electronic neural network has been trained, using the training corpus of training supra-images and on an electronic computer, to determine the presence of the pathology property in a supra-image by:

randomly sampling collections of components corresponding to images from individual training supra-images, whereby a plurality of collections of components are obtained;

labeling the collections of components according to a respective electronic label for their respective supra-image, whereby a plurality of weakly labeled collections of components are obtained from the plurality of collections of components; and iteratively training, through the plurality of weakly labeled collections of components, the electronic neural network to determine the presence of the pathology property.

7. The method of claim 1, wherein the evaluation supra-image and a plurality of the training supra-images represent biopsies.

8. The method of claim 1, wherein each image of a plurality of the training supra-images comprises a whole-slide image, wherein the evaluation supra-image comprises at least one whole-slide image.

9. The method of claim 1, wherein each component comprises a feature vector.

10. The method of claim 1, wherein the pathology property comprises one of: a presence of a malignancy, a presence of a specific grade of malignancy, or a presence of a category of risk.

11. A system for determining a presence of a pathology property in a supra-image, the system comprising:

a processor; and a memory communicatively coupled to the processor, the memory storing instructions which, when executed on the processor, perform operations comprising:

receiving an electronic evaluation supra-image, wherein the electronic evaluation supra-image comprises constituent images of a same specimen;

providing the electronic evaluation supra-image to an electronic neural network that has been trained, using a training corpus of training supra-images and on an electronic computer, to determine the presence of the pathology property in a supra-image, each training supra-image comprising at least one image of a same specimen, each image corresponding to a plurality of components, wherein a respective component comprises a tile of an image or a feature vector representative of the tile, wherein each training supra-image of the training corpus is associated with a respective electronic label indicating whether the pathology property is present, wherein the training corpus is sufficient to train the electronic neural network to determine a presence of the pathology property;

receiving from the electronic neural network an output indicative of whether the pathology property is present in the evaluation supra-image; and providing the output.

12. The system of claim 11, wherein the electronic computer comprises volatile electronic memory having a storage capacity, wherein a probability that the pathology property is present in at least one component of a sampled collection of components of images of at least one training supra-image of the training corpus indicates that the training corpus is sufficient to train the electronic neural network to determine the presence of the pathology property, wherein the storage capacity of the volatile electronic memory is sufficient to store the sampled collection of components simultaneously.

13. The system of claim 12, wherein the operations further comprise:

obtaining, for each respective component of each image of the at least one training supra-image of the training corpus, a respective electronic label indicating whether the pathology property is present in the respective component, whereby a plurality of labels is obtained;

wherein the probability is based on at least the plurality of labels.

14. The system of claim 13, wherein the operations further comprise:

calculating, based on at least the plurality of labels, the probability; and determining, based on at least the probability, that the training corpus is sufficient to train the electronic neural network to determine the presence of the pathology property.

15. The system of claim 12, wherein the probability comprises:

$$1 - \frac{n_{neg}! \, (N - n_{RAM})!}{N! \, (n_{neg} - n_{RAM})!}$$

wherein N represents a number of components of the sampled collection of components, $n_{neg}$ represents a number of components of the sampled collection of components that lack the pathology property, and $n_{RAM}$ represents a maximum number of components that can be simultaneously stored in the volatile electronic memory.

16. The system of claim 11, wherein the electronic neural network has been trained, using the training corpus of training supra-images and on an electronic computer, to determine the presence of the pathology property in a supra-image by:

randomly sampling collections of components corresponding to images from individual training supra-images, whereby a plurality of collections of components are obtained;

labeling the collections of components according to a respective electronic label for their respective supra-image, whereby a plurality of weakly labeled collections of components are obtained from the plurality of collections of components; and iteratively training, through the plurality of weakly labeled collections of components, the electronic neural network to determine the presence of the pathology property.

17. The system of claim 11, wherein the evaluation supra-image and a plurality of the training supra-images represent biopsies.

18. The system of claim 11, wherein each image of a plurality of the training supra-images comprises a whole-slide image, wherein the evaluation supra-image comprises at least one whole-slide image.

19. The system of claim 11, wherein each component comprises a feature vector.

20. The system of claim 11, wherein the pathology property comprises one of: a presence of a malignancy, a presence of a specific grade of malignancy, or a presence of a category of risk.

* * * * *